(12) United States Patent
Rybak et al.

(10) Patent No.: US 6,395,276 B1
(45) Date of Patent: May 28, 2002

(54) IMMUNOTOXINS DIRECTED AGAINST MALIGNANT CELLS

(75) Inventors: Susanna M. Rybak, Frederick; Dianne L. Newton, Rockville, both of MD (US); David M. Goldenberg, Mendham, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

(21) Appl. No.: 09/071,672

(22) Filed: May 1, 1998

Related U.S. Application Data

(60) Provisional application No. 60/046,895, filed on May 2, 1997.

(51) Int. Cl.$^7$ .................. A61K 39/395; A61K 38/00; A61K 39/385; A61K 39/00; C12P 21/08

(52) U.S. Cl. ................ 424/179.1; 424/134.1; 424/141.1; 424/178.1; 424/183.1; 424/192.1; 424/193.1; 514/12; 514/44; 530/387.3; 530/391.7

(58) Field of Search ............ 530/387.3, 391.7; 424/134.1, 141.1, 183.1, 178.1, 179.1, 192.1, 193.1; 514/12, 44

(56) References Cited

U.S. PATENT DOCUMENTS

| | | | |
|---|---|---|---|
| 4,816,567 A | 3/1989 | Cabilly et al. | 530/387 |
| 5,559,212 A | 9/1996 | Wojciech | 530/350 |
| 5,728,805 A | 3/1998 | Wojciech | 530/350 |
| 5,840,840 A | * 11/1998 | Rybak et al. | |
| 5,995,073 A | * 9/1999 | Rybak et al. | |
| 6,083,477 A | * 7/2000 | Goldenberg | |

FOREIGN PATENT DOCUMENTS

| | | | |
|---|---|---|---|
| EP | 0 173 494 A2 | 7/1985 | C12N/15/00 |
| WO | WO 87/02671 | 10/1986 | C07H/15/12 |
| WO | WO 88/09344 A | 5/1988 | C07K/13/00 |
| WO | WO 97/02588 | 6/1996 | H01J/37/32 |
| WO | PCT/US98/05453 | 3/1998 | |

OTHER PUBLICATIONS

Rybak et al. PNAS, 89:3165–3169, 1992.*
De Prisco, et al., A Ribonuclease from human seminal plasma active on double–stranded RNA, *Biochim. Biophys. Acta* 788:356–363 (1984).
Jones, et al., "Replacing the complementarity–determining regions in a human antibody with those from a mouse," *Nature* 321:522–525 (May 29, 1986).
Williams, et al., "Production of antibody–tagged enzymes by myeloma cells: application to DNA polymerase I Klenow fragment" *Gene* 43:319–324 (1986).
St. Clair, et al., "Angiogenin abolishes cell–free protein synthesis by specific ribonucleolytic inactivation of ribosomes," *Proc. Natl. Acad. Sci. USA* 84:8330–8334 (12/87).

Riechmann, et al., "Reshaping human antibodies for therapy," *Nature* 332:323–327 (Mar. 24, 1988).
Huston, et al., "Protein engineering of antibody binding sites: Recovery of specific activity in an anti–digoxin single–chain Fv analogue produced in *Escherichia coli*," *Proc. Natl. Acad. Sci. USA* 85:5878–5883 (8/88).
Bird, et al., "Single–chain antigen–binding proteins," *Science* 242:423–426 (Oct. 21, 1998).
Darzynkiewicz, et al., "Cytostatic and Cytotoxic effects of Pannon (P–30 Protein), a novel anticancer agent," *Cell Tissue Kinet.* 21:169–182 (1988).
Khazaeli, et al., "Immunology," *Proceedings of AACR* 29:418 (1988).
Nishimura, et al., "Expression and function of a CD 5 cDNA in human and murine T cells," *Eur. J. Immunol.* 18:747–753 (1988).
Griffin, et al., "Immunotoxin therapy: Assessment by animal models," *Immunotoxins*, Boston/Dordrecht/Lancaster, Kluwer Academic Publishers, p. 433–455 (1988).
Chaudhary, et al., "A recombinant immunotoxin consisting of two antibody variable domains fused to Pseudomonas exotoxin," *Nature* 339:394–397 (Jun. 1, 1989).
Ward, et al., "Binding activities of a repertoire of single immunoglobulin variable domaines secreted from *Escherichia coli*," *Nature* 341:544–546 (Oct. 12, 1989).
Batra, et al., "Antitumor activity in mice of an immunotoxin made with anti–transferrin receptor and a recombinant form of Pseudomonas exotoxin," *Proc. Natl. Acad. Sci. USA* 86:8545–8549 (11/89).
Mikulski, et al., "Striking increase of survival of mice bearing M109 madison charcinoma treated with a novel protein from amphibian embryos," *J. Nat'l. Cancer Inst.* 82(2):151–153 (Jan. 17, 1990).
Chaudhary, et al., "A rapid method of cloning functional variable–region antibody genes in *Escherichia coli* as single–chain immunotoxins," *Proc. Natl. Acad. Sci. USA* 87:1066–1070 (2/90).
Casadei, et al., "Expression and secretion of aequorin as a chimeric antibody by means of a mammalian expression vector," *Proc. Natl. Acad. Sci. USA* 87:2047–2051 (3/90).
Goodson, et al., "Site–directed pegylation of recombinant interleukin–2 at its glycosylation site," *Bio/Technology* 8:343–346 (4/90).
Batra, et al., "Anti–tac (Fv)–PE40, a single chain antibody Pseudomonas fusion protein directed at interleukin 2 receptor bearing cells," *J. Biol. CHem.* 265:15198–15202 (Sep. 5, 1990).

(List continued on next page.)

*Primary Examiner*—David Saunders
*Assistant Examiner*—Amy DeCloux

(57) ABSTRACT

The present invention relates to immunotoxins, that effectively kill malignant cells having a given surface marker and nucleic acid constructs encoding them. These reagents comprise a toxic moiety that is derived from a *Rana pipiens* protein having ribonucleolytic activity linked to an antibody capable of specific binding with a chosen tumor cell.

8 Claims, 9 Drawing Sheets

OTHER PUBLICATIONS

Mikulski, et al., "Tamoxifen and trifluoroperazine (Stelazine) potentiate cytostatic/cytotoxic effects of P–30 protein, a novel protein possessing anti–tumour activity," *Cell Tissue Kinet.* 23:237–246 (1990).

Winter, et al., "Man–made antibodies," *Nature* 349:293–299 (Jan. 24, 1991).

Rybak, et al., "Human Cancer Immunology II. Clinical use of immunotoxins. Monoclonal antibodies conjugated to protein toxins," *Immunology and Allergy Clinics of North America* 11(2):359–380, W.B. Saunders Co. (5/91).

Pearson, J.W., et al., "Reversal of Drug Resistance in a Human Colon Cancer Xenograft Expressing MDR1 Complementary DNA by in vivo administration of MRK–16 monoclonal Antibody," *J. Natl. Cancer Inst.* 83(19):1386–1391 (Oct. 2, 1991).

Ghetie, et al., "Antitumor activity of Fab' and IgG–anti–CD22 immunotoxins in disseminated Human B lymphoma grown in mice with severe combined immunodeficiency disease: effect on tumor cells in extranodal sites," *Cancer Res.* 51:5876–5880 (Nov. 1, 1991).

Hoogenboom, et al., "Construction and expression of antibody–tumor necrosis factor fusion proteins," *Molecular Immunology* 28(9):1027–1037 (Nov. 4, 1991).

Rybak, et al., "Cytotoxic potential of ribonuclease and ribonuclease hybrid proteins," *J. Biol. Chem.* 266:21202–21207 (Nov. 5, 1991).

Hoogenboom, et al., "Targeting of tumor necrosis factor to tumor cells: secretion by myeloma cells of a genetically engineered antibody–tumor necrosis factor hybrid molecule," *Biochim. Biophys. Acta* 1096:345–354 (Nov. 20, 1991).

Ardelt, et al., "Amino acid sequence of an anti–tumor protein from *Rana pipiens* oocytes and early embryos," *J. Biol. Chem.* 266(1):245–251 (1991).

Uckun, et al., "In vivo efficacy of B43 (anti–CD19)–pokeweed antiviral protein immunotoxin against human Pre–B cell acute lymphoblastic leukemia in mice with severe combined immunodeficiency," *Blood* 79(9):2201–2214 (May 1, 1992).

Newton, et al., "Cytotoxic ribonuclease chimeras," *J. Biol. CHem.* 267(27):19572–19578 (Sep. 25, 1992).

Grossbard, et al., "Anti–B4–blocked ricin: A phase I trial of 7–day continuous infusion in patients with B–cell neoplasms," *J. Clin. Oncol.* 11(4):726–737 (4/93).

Grossbard, et al., "Adjuvant immunotoxin therapy with anti–B4–blocked ricin after autologous bone marrow transplantation for patients with B–cell non–Hodgkin's lymphoma," *Blood* 81(9):2263–2271 (May 1, 1993).

Amlot, et al., "A Phase I study of an anti–CD22–deglycosylated ricin A chain immunotoxin in the treatment of B–cell lymphomas resistant to conventional therapy," *Blood* 82(9):2624–2633 (Nov. 1, 1993).

Rybak, et al. "Cytotoxic onconase and ribonuclease A chimeras: Comparison and in Vitro characterization," *Drug Delivery* 1:3–10 (1993).

Newton, et al., "Toxicity of an antitumor ribonuclease to Purkinje neurons," *J. Neurosci.* 14(2): 538–544 (2/94).

Rybak, et al., "RNase and RNase immunofusions for cancer therapy," *Tumor Targeting* 1(3):141–147 (1995).

Francisco, et al., "Activity of a single–chain immunotoxin that selectively kills lymphoma and other B–lineage cells expressing the CD40 antigen," *Cancer Res.* 55:3099–3104 (Jul. 15, 1995).

Sausville, et al., "Continuous infusion fo the anti–CD22 immunotoxin IgG–RFB4–SMPT–dgA in patients with B–cell lymphoma: A Phase I study," *Blood* 85(12):3457–3465 (Jun. 15, 1995).

Mansfield, et al., "Characterization of RFB4–Pseudomonas exotoxin A immunotoxins targeted to CD22 on B–cell malignancies," *Bioconj. Chem.* 7:557–563 (1996).

Newton, D.L., et al., "Anti–tumor ribonuclease, combined with or conjugated to monoclonal antibody MRK16, overcomes multidrug resistance to vincrinstine in vitro and in vivo," *Int'l. Oncology* 8:1095–1104 (1996).

Newton, D.L., et al., "Angiogenin single–chain immunofusions: influence of peptide linkers and spacers between fusion protein domains," *Biochemistry* 35:545–553 (1996).

Mansfield, et al., "Recombinant RFB4 immunotoxins exhibit potent cytotoxic activity for CD22–bearing cells and tumors," *Blood* 90(5):2020–2026 (Sep. 1, 1997).

Mansfield, et al., "Recombinant RFB4 single–chain immunotoxin that is cytotoxic towards CD22–positive cells," *Biochem. Soc. Trans.* 25:709–714 (1997).

* cited by examiner

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 104 amino acids
      (B) TYPE: amino acid
      (C) STRANDEDNESS:
      (D) TOPOLOGY: linear (ii) MOLECULE TYPE: protein (ix) FEATURE:
      (A) NAME/KEY: Modified-site
      (B) LOCATION: 1
      (D) OTHER INFORMATION: /product= "OTHER" /note= "Xaa = Glu or
          pyroglutamic acid"

(ix) FEATURE:
      (A) NAME/KEY: Protein (B) LOCATION: 1..104
    (D) OTHER INFORMATION: /note= "RNase A derived from Rana
        pipiens, "onc protein""

(xi) SEQUENCE DESCRIPTION: SEQ ID NO:1:

Xaa Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
            85                  90                  95

His Phe Val Gly Val Gly Ser Cys
            100

(2) INFORMATION FOR SEQ ID NO:2:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..249
        (D) OTHER INFORMATION: /note= "nucleic acid encoding "onc
            protein""

(xi) SEQUENCE DESCRIPTION: SEQ ID NO:2:

GATGTTGATT GTGATAATAT CATGTCAACA AACTTGTTCC ACTGCAAGGA CAAGAACACT      60

TTTATCTATT CACGTCCTGA GCCAGTGAAG GCCATCTGTA AAGGAATTAT AGCCTCCAAA     120

AATGTGTTAA CTACCTCTGA GTTTTATCTC TCTGATTGCA ATGTAACAAG CAGGCCTTGC     180

AAGTATAAAT TAAAGAAATC AACTAATAAA TTTTGTGTAA CTTGTGAAAA TCAGGCACCA     240

GTTCATTTT                                                            249

(2) INFORMATION FOR SEQ ID NO:3:

(i) SEQUENCE CHARACTERISTICS:
        (A) LENGTH: 83 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..83
        (D) OTHER INFORMATION: /note= ""onc protein", positions 16-98
            of SEQ ID NO:1"

(xi) SEQUENCE DESCRIPTION: SEQ ID NO:3:

Asp Val Asp Cys Asp Asn Ile Met Ser Thr Asn Leu Phe His Cys Lys
1               5                   10                  15

Asp Lys Asn Thr Phe Ile Tyr Ser Arg Pro Glu Pro Val Lys Ala Ile

-continued

```
                    20                  25                  30
Cys Lys Gly Ile Ile Ala Ser Lys Asn Val Leu Thr Thr Ser Glu Phe
            35                  40                  45

Tyr Leu Ser Asp Cys Asn Val Thr Ser Arg Pro Cys Lys Tyr Lys Leu
        50                  55                  60

Lys Lys Ser Thr Asn Lys Phe Cys Val Thr Cys Glu Asn Gln Ala Pro
65                  70                  75                  80

Val His Phe
```

IMMUNOTOXINS DIRECTED AGAINST MALIGNANT CELLS

CROSS-REFERENCE TO RELATED APPLICATIONS

This application is a continuation of and claims priority to U.S. Provisional Application 60/046,895, filed May 2, 1997. The disclosure of the following U.S. Provisional Patent Application is incorporated herein by reference in its entirety: S. M. Rybak and D. L. Newton, "Recombinant Anti-Tumor RNAse," filed Mar. 27, 1998

FEDERALLY SPONSORED RESEARCH OR DEVELOPMENT

Not applicable.

BACKGROUND OF THE INVENTION

Toxic enzymes from plants and bacteria such as ricin, diphtheria toxin and Pseudomonas toxin have been coupled to antibodies or receptor binding ligands to generate cell-type-specific-killing reagents (Youle, et al., *Proc. Nat'l Acad. Sci. USA*77:5483 (1980); Gilliland, et al., *Proc. Nat'l Acad. Sci. USA*77:4539 (1980); Krolick, et al., *Proc. Nat'l Acad. Sci. USA*77:5419 (1980)). Regardless of the fact that the cell-recognition moiety is not always an antibody, these directed toxins are generally known as immunotoxins. These hybrid proteins kill cells which express the receptor or cell surface marker that the antibody or ligand portion of the molecule recognizes.

Under appropriate conditions, depending on the particular receptor or cell surface marker, the toxin enters the cytosol, inactivates the protein synthesis machinery and causes death of the target cell. Immunotoxins, which have been shown to be highly cytotoxic to cancer cells growing in cell culture and in animal models, demonstrate the potential of these reagents to treat blood and lymph borne malignancies which, because of their dissemination are not treatable by traditional surgical techniques, as well as solid tumors in restricted compartments such as the intraperitoneal cavity (reviewed in Griffin, et al., IMMUNOTOXINS, p 433, Boston/Dordrecht/Lancaster, Kluwer Academic Publishers, (1988); Vitetta, et al., *Science*238:1098 (1987); Fitzgerald, et al., *J. Nat'l Cancer Inst.* 81:1455 (1989)). Traditional chemotherapies, while being effective in the treatment of some cancerous conditions, exhibit undesired side effects due to the systemic toxicity of the chemotherapeutic compounds.

An ideal candidate for cancer therapy, therefore, would be an immunotoxin that would selectively be cytotoxic to cancer cells yet remain harmless to non-cancerous cells of the patient. Utilization of this type of anti-tumor therapy, however, has been stymied by the development of immune responses in patients to foreign proteins which comprise the immunotoxins. Immune responses against murine monoclonal antibodies (Sawler, et al., *J. Immunol.* 135:1530 (1985); Schroff, et al., *Cancer Res.* 45:879 (1985)) and anti-toxin antibodies have been detected in both animals and humans treated with immunotoxins (Rybak, et al., *Immunol. and Allergy Clinics of North America*11(2):359 (1991); Harkonen, et al., *Cancer Res.* 47:1377 (1987); Hertler, A. in IMMUNOTOXINS p. 475, Kluwer Academic Publishers, Boston/Dordrecht/Lancaster (1988)). Advances in humanization techniques have alleviated some of the immunogenicity associated with the antibody portion of immunotoxins (Bird, et al., *Science*242:423 (1988); Huston, et al., *Proc. Nat'l Acad. Sci. USA*85:5879 (1988); Ward, et al., *Nature*341:544 (1989); and Jones, et al., *Nature*314:522 (1986)). However, no solution has been found to counter the immunogenicity of the toxic moiety other than immunosuppression of the patients (Khazaeli, et al., *Proceedings of AACR*29:418 (1988)). Thus, there has been a continuing need for methods and compositions that would reduce the immunogenicity of the toxic moiety of immunotoxins yet retain the ability to selectively kill cells having a given surface marker.

B-cell lymphomas fall under the generic rubric of non-Hodgkin's lymphomas and can either be a disseminated or a solid tumor within the lymph system. Radiolabeled humanized murine antibodies which have been raised against CD22 (LymphoCide™), a surface marker on malignant B cells, are currently in clinical trials as a treatment for B-cell lymphomas (Immunomedics, Inc., Press Release, http://www.immunomedic.com/ theral.html). See also, Amlot, et al., *Blood*82:2624–2633 (1993); Sausville, et al., *Blood*85:3457–3465 (1995); Grossbard, et al., *Blood*81:2263–2271 (1993); Grossbard, et al., *Clin. Oncol.* 11:726–737 (1993). To date, some antitumor responses have been noted but immunotoxin-mediated toxicity to normal tissue often prevented dosing at therapeutic levels. In addition to CD22, several B-cell-specific antigens such as CD 19 and CD40 have been targeted by immunotoxins made with plant toxins such as ricin A-chain and bacterial toxins, such as Pseudomonas exotoxin A (PE). Uckun, et al., *Blood*79:2201–2214 (1992); Ghetie, et al., *Cancer Res.* 51:5876–5880 (1991); Francisco, et al., *Cancer Res.* 55:3099–3104 (1995).

The cytotoxicity of RNase A toward tumor cells is well documented from studies performed in the 1960s and 1970s. Early work is reviewed in Roth, *Cancer Res.* 23:657 (1963). The relevance of these early studies has been sustained by the discovery that an anti-tumor protein from oocytes of *Rana pipiens* is homologous to bovine pancreatic RNase A (Ardelt, et al., *J Biol. Chem.* 256:245 (1991)). P-30 protein (and referred to herein as the onc protein) was isolated from extracts of *Rana pipiens* early embryos based upon anti-proliferative/cytotoxic effects toward cancer cells in vitro (Darzynkiewicz, et al., *Cell Tissue Kinet.* 21:169 (1988); Mikulski, et al., *Cell Tissue Kinet.* 23:237 (1990)) and in animal models (Mikulski, et al.,*J. Nat l. Cancer Inst.* 82:151 (1990)). Phase III human clinical trials of the onc protein in patients with a variety of solid tumors are currently in progress.

SUMMARY OF THE INVENTION

The present invention relates to immunotoxins, that are useful for killing malignant B cells and other malignant cells and are directed to a surface marker on B cells and the nucleic acid constructs encoding the immunotoxins. These reagents comprise a toxic moiety that is derived from a *Rana pipiens* protein having ribonucleolytic activity linked to an antibody capable of specific binding with a chosen tumor cell.

We have found that these particular immunotoxins had highly surprising properties as they were up to 2000fold more active against malignant B cells than their human RNase counterparts or than the toxin itself. Further, as will be described in more detail below, their use when administered in vivo against disseminated tumors, resulted in dramatically lowered side effects. These highly effective, but apparently non-toxic, immunotoxins directed against such ubiquitous diseases as B cell lymphomas present a new and exciting therapeutic option for patients suffering from such diseases.

It is an object of the present invention to provide cytotoxic RNase (onc protein) immunotoxins that selectively kill cells having a given surface marker. These immunotoxins are minimally immunogenic and generate less systemic toxicity than presently known immunotoxins. In particular, it is an object of the present invention to provide direct immunotoxins comprising protein fragments with ribonucleolytic activity linked to humanized antibodies that recognize specific markers on tumor cells.

In another embodiment, the present invention relates to a pharmaceutical composition comprising an immunotoxin of the present invention and a pharmaceutically acceptable carrier.

In a further embodiment, the present invention relates to a method selectively killing cells. The method comprises contacting the tumor cells to be killed with a selective immunotoxin of the present invention under conditions such that the monoclonal antibody binds to a surface marker on the tumor cell thereby causing the toxic onc protein to kill the cell.

Various other objects and advantages of the present invention will be apparent from the following description of the invention.

DESCRIPTION OF THE FIGURES

FIG. 5A shows the percentage of RNase material retained in the cells and FIG. 5B shows the percentage of PNase material degraded and released into the supernatant.

DETAILED DESCRIPTION OF THE INVENTION

Figure 1:
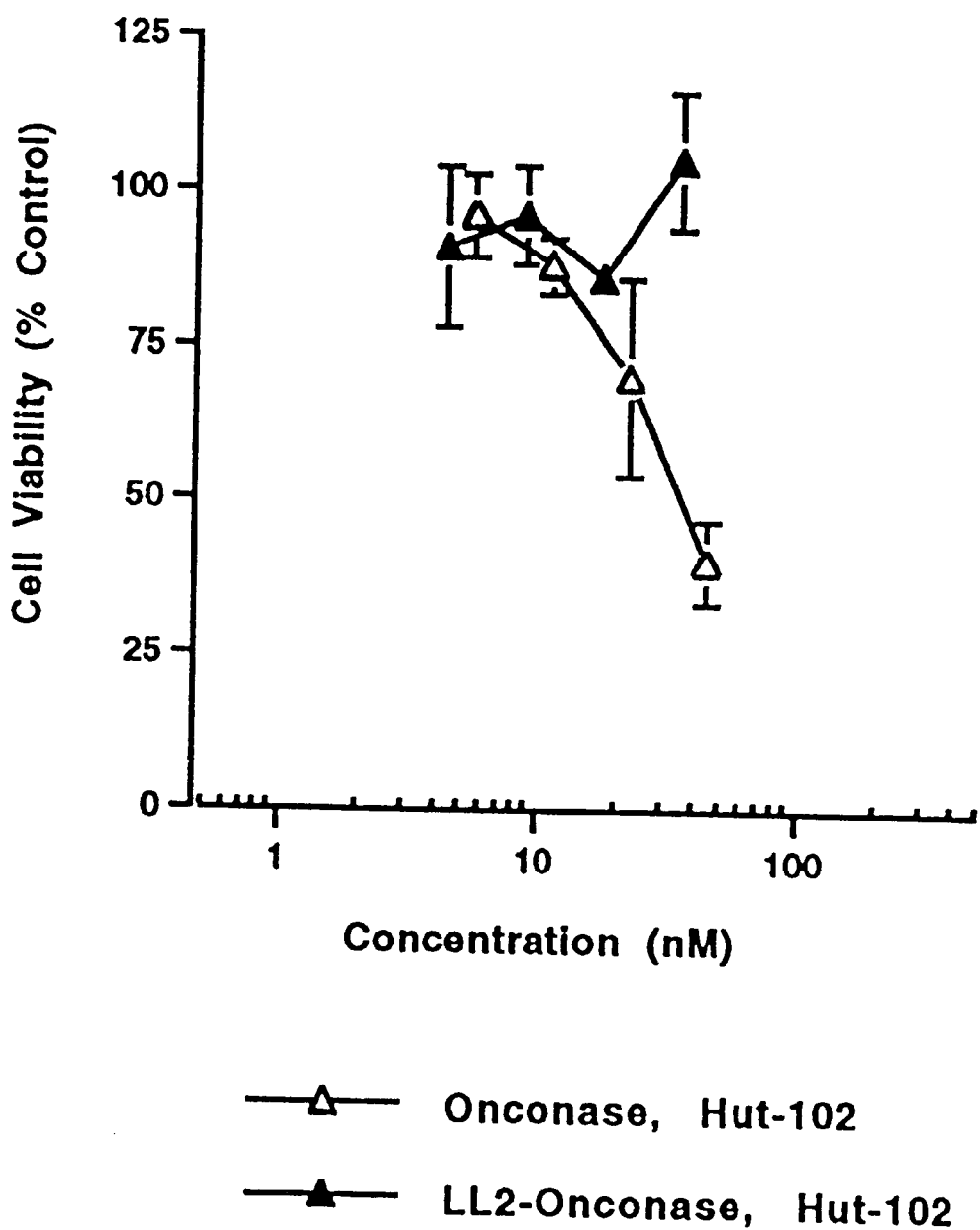
FIG. 1 indicates that ONCONASE® is more cytotoxic to HUT 102 T cell lymphoma cells (which do not bear the CD22 marker recognized by LL2) than the immunotoxin, LL2-ONCONASE®.

The present invention relates to the use of an RNase protein, particularly an RNase derived from *Rana pipiens* as a toxic moiety in a directed immunotoxin to B cells. Immunotoxic reagents of the present invention comprise a protein and an antibody that specifically binds to a chosen tumor cell surface marker. In studies detailed below, the onc protein is shown to be far superior to other immunotoxins that comprise antibodies directed against CD22 or CD74 and a human non-toxic RNase. The onc protein-based immunotoxins are powerful agents against malignant B cells, such as B cell lymphomas and leukemias and other malignancies, such as neuroblastoma.

DEFINITIONS

The term "antibody" or "antibody peptide(s)" refers to polyclonal and monoclonal antibodies, an entire immunoglobulin or antibody or any functional fragment of an immunoglobulin molecule which binds to the target antigen and is defined further below. Examples of such functional entities include complete antibody molecules, antibody fragments, such as Fv, single chain Fv, complementarity determining regions ($CDR_s$), $V_L$ (light chain variable region), $V_H$ (heavy chain variable region), Fab, F(ab)$_2$' and any combination of those or any other functional portion of an immunoglobulin peptide capable of binding to target antigen.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$ a dimer of Fab which itself is a light chain joined to $V_H$–$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, FUNDAMENTAL IMMUNOLOGY, 3RD ED., W. E. Paul, ed., Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

For this invention, an antibody, is "reactive with" or "binds to" an antigen if it interacts with the antigen. This interaction is analogous to a chemical reaction in which two reactants come together to form a product. In the case of the antibody-antigen interaction, the product of the interaction is an antibody-antigen complex. The preferred antigens which bind to immunoglobulins of the invention are the CD22 and the CD74 cell surface marker.

The term "binding specificity," "specifically binds to an antibody" or "specifically immunoreactive with," when referring to a protein or carbohydrate, refers to a binding reaction which is determinative of the presence of the protein or carbohydrate in the presence of a heterogeneous population of proteins and other biologics. Thus, under designated immunoassay conditions, the specified antibodies bind to a particular protein or carbohydrate and do not bind in a significant amount to other proteins or carbohydrates present in the sample. Specific binding to an antibody under such conditions may require an antibody selected for its specificity towards a particular protein or carbohydrate. For example, antibodies raised to the CD22 antigen may be selected to provide antibodies that are specifically immunoreactive with CD22 protein and not with other proteins. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See Harlow & Lane, ANTIBODIES, A LABORATORY MANUAL, Cold Spring Harbor Publication, New York (1988) for a description of immunoassay formats and conditions that can be used to determine specific immunoreactivity.

The term "humanized" refers to an antibody wherein the constant regions have at least about 80% or greater homology to human immunoglobulin. Additionally, some of the nonhuman, such as murine, variable region amino acid residues can be modified to contain amino acid residues of human origin.

Humanized antibodies have been referred to as "reshaped" antibodies. Manipulation of the complementarity-determining regions (CDR) is a way of achieving humanized antibodies. See, for example, Jones, et al., *Nature* 321:522 (1988) and Riechmann, et al., *Nature* 332:323 (1988), both of which are incorporated by reference herein. For a review article concerning humanized antibodies, see Winter & Milstein, *Nature* 349:293 (1991), incorporated by reference herein.

The terms "isolated" or "substantially purified," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

In particular, an isolated onc protein gene is separated from open reading frames which flank the gene and encode proteins other than onc protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. The term "nucleic acid" refers to a deoxyribonucleotide or ribonucleotide polymer in either single-or double-stranded form, and unless otherwise limited, would encompass known analogs of natural nucleotides that can function in a similar manner as naturally occurring nucleotides.

The term "joined" in the context of the immunotoxins of this invention encompasses the linking of moieties (typically an antibody and a toxin) through covalent bonding, including disulfide bonding; hydrogen bonding; electrostatic bonding; recombinant fusion; and conformational bonding, e.g., antibody-antigen, and biotin-avidin associations.

The terms "measurable ribonucleolytic activity" or "significant ribonucleolytic activity" refer to a molecule which has an $IC_{50}$ of less than 40 ng/mL when added to a rabbit reticulocyte lysate assay wherein protein synthesis is inhibited as measured by the incorporation of [$^{35}$S]methionine into acid precipitable protein. $IC_{50}$ is the concentration of protein necessary to inhibit protein synthesis by 50% in the assay. The lysate assay may be done as described in the Promega lysate assay kit which is commercially available from Promega Corporation, Madison, Wis. Ribonucleolytic activity using high molecular weight RNA and tRNA is determined at 37° C. through the formation of perchloric acid soluble nucleotides following published protocols (Newton, D. L., et al. *Biochemistry* 35:545–553 (1996)). With poly(A,C) UpG and poly U, ribonucleolytic activity is assayed according to DePrisco, et al., and Libonati & Floridi (DePrisco, R., et al. *Biochimica et Biophysica Adcta* 788:356–363 (1984); Libonati, M. et al. *European J Biochem.* 8:81–87 (1969)). Activity is assayed by measuring the increase with time in absorbance at 260 nm. Incubation mixtures (1 mL of 10 mM imidazole, 0.1 M NaCl, pH 6.5 or pH 7) contain substrate and appropriate amounts of enzyme solution at 25° C. The in vitro translation assay (St. Clair, D. K., et al. *Proc. Nat 'l Acad. Sci. USA* 84:8330–8334 (1987)) and the cell viability assays using the (3-[4,5-dimethylthiazol-2-yl]-2,5-diphenyltetrazolium bromide; Thiazolyl blue; MTT) (Mossman, T. *J Inmmunol. Methods* 65:55–63 (1983)) are performed as previously described (Pearson, J. W., et al. *J. Nat'l CancerInst.* 83:1386–1391 (1991)).

The term "nucleic acid encoding" or "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both full length nucleic acid sequences as well as shorter sequences derived from the full length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex form.

The term "onc protein" refers to an RNase A derived from *Rana pipiens* that was originally designated P-30 protein and first described in Darzynkiewicz, et al., *Cell Tissue Kinet.* 21:169 (1988), such as the protein having the sequence set out in SEQ ID NO:1. A description of this protein can be found in U.S. Pat. No. 5,559,212. The term "native onc protein" refers to the protein in its native form, purified from *Rana pipiens* oocytes. The term "recombinant onc protein" refers to the protein produced by recombinant means. Preferred embodiments of these recombinant proteins and their nucleic sequences are described in PCT Application No: PCT/US97/02588. It is understood that onc proteins also encompass modifications in both the nucleic acid and the amino acid sequences but have measurable ribonucleolytic activity.

An "onc-derived" amino acid sequence includes one that contains at least one string of six contiguous amino acids identical to a contiguous sequence of six amino acids selected from the group of sequences beginning at amino acid positions 1 (with Glu replacing pyroglu), 2, 3, 4, 5, 6, 7, 8, 11, 12, 13, 14, 15, 16, 18, 19, 20, 22, 23, 24, 25, 26, 27, 28, 29, 30, 31, 32, 33, 34, 35, 36, 37, 41, 42, 43, 44, 45, 46, 47, 50, 52, 54, 56, 59, 60, 25 61, 62, 63, 64, 65, 66, 67, 68, 69, 70, 71, 72, 73, 74, 76, 80, 81, 82, 84, 85, 86, 87, 91, 92, 93, 95, or 96 of the one amino acid sequence (SEQ ID NO:1).

The term "pharmaceutical composition" refers to formulations of various preparations. Parenteral formulations are known and are preferred for use in the invention. The formulations containing therapeutically effective amounts of the immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg or more.

Typically, the pharmaceutical compositions containing the immunotoxins are administered in a therapeutically effective dose over either a single day or several days by daily intravenous infusion.

The immunotoxins of this invention may be administered systemically by injection, most preferably intravenously, but also intramuscularly, subcutaneously, intrathecally, intraperitoneally, into vascular spaces, or into joints, e.g., intraarticular injection. The dose will be dependent upon the properties of the immunotoxin employed, e.g., its activity and biological half-life, the concentration of the immunotoxin in the formulation, the site and rate of dosage, the clinical tolerance of the patient involved, the extent of cancer afflicting the patient and the like as is well within the skill of the physician.

The immunotoxin of the present invention may be administered in solution. The pH of the solution should be in the range of pH 5 to 9.5, preferably pH 6.5 to 7.5. The immunotoxins or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of the immunoglobulin may also contain a salt, such as sodium chloride or potassium chloride in a concentration of 50 to 150 mM. An effective amount of a stabilizing agent such as albumin, a globulin, a detergent, a gelatin, a protamine or a salt of protamine may also be included and may be added to a solution containing the immunotoxin or to the composition from which the solution is prepared. Systemic administration of the immunotoxin is typically made every two to three days or once a week if a humanized form of the antibody is used. Alternatively, daily administration is useful. Usually administration is by either intramuscular injection or intravascular infusion.

Administration may also be intranasal or by other non-parenteral routes. The immunotoxin may also be administered via microspheres, liposomes or other microparticulate delivery systems placed in certain tissues including blood.

The immunotoxin may also be administered by aerosol to achieve localized delivery to the lungs. This is accomplished by preparing an aqueous aerosol, liposomal preparation or solid particles containing or derivatives thereof. A nonaqueous (e.g., fluorocarbon propellent) suspension could be used. Sonic nebulizers preferably are used in preparing aerosols. Sonic nebulizers minimize exposing the antibody or derivatives thereof to shear, which can result in degradation of the immunotoxin.

Ordinarily, an aqueous aerosol is made by formulating an aqueous solution or suspension of the immunotoxin together with conventional pharmaceutically acceptable carriers and stabilizers. The carriers and stabilizers will vary depending upon the requirements for the particular immunotoxin, but typically include nonionic surfactants (TWEEN-20 OR -80®, PLURONIC-F128 OR -67®, or polyethylene glycol), innocuous proteins like serum albumin, or sorbitan esters, oleic acid, lecithin, amino acids such as glycine, buffers, salts, sugars or sugar alcohols. The formulations will be sterile. Aerosols generally will be prepared from isotonic solutions.

The terms "recombinant DNA," "recombinant nucleic acid" or "recombinantly produced DNA" refer to DNA which has been isolated from its native or endogenous source and modified either chemically or enzymatically by adding, deleting or altering naturally-occurring flanking or internal nucleotides. Flanking nucleotides are those nucleotides which are either upstream or downstream from the described sequence or sub-sequence of nucleotides, while internal nucleotides are those nucleotides which occur within the described sequence or subsequence.

The term "recombinant means" refers to techniques where proteins are isolated, the CDNA sequence coding the protein identified and inserted into an expression vector. The vector is then introduced into a cell and the cell expresses the protein. Recombinant means also encompasses the ligation of coding or promoter DNA from different sources into one vector for expression of a fusion protein, constitutive expression of a protein, or inducible expression of a protein.

The terms "recombinant protein," "recombinantly produced protein" or "recombinantly produced immunotoxin" refer to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The term "selective cytotoxic reagent" refers to a compound that when added to a population of different cells, e.g., within an organism, kills one type of cell in the population based on some physical characteristic of the cell, i.e., a surface ligand or marker to which the cytotoxic reagent binds and then becomes internalized.

The term "single chain antibody" refers to an antibody wherein the genetic information encoding the functional fragments of the antibody are located in a single contiguous length of DNA. For a thorough description of single chain antibodies, see Bire, et al., *Science*242:423 (1988) and Huston, et al., *Proc. Nat'l Acad. Sci. USA*85:5879 (1988).

The term "surface marker" refers to a protein, carbohydrate, or glycoprotein present on the surface of a cell. Different types of cells express different cell surface markers and therefore cells can be identified by the presence of a cell surface marker. For example, malignant B cells overexpress CD22. Thus, the binding of an antibody that recognizes CD22 identifies that cell as a B cell. CD74, described below, is an example of a cell surface marker found on B cells and a select group of other malignant cells.

Among various uses of the immunotoxins of the present invention are included a variety of disease conditions caused by specific human cells that may be eliminated by the toxic action of the protein. One preferred application for the immunoconjugates of the invention is the treatment of malignant B cells expressing CD22. Exemplary malignant diseases of B cells include acute lymphocytic leukemia (ALL), chronic B-lymphocytic leukemia (B-CLL), chronic myelogenous leukemia, Burkitt's, AIDS-associated and Follicular lymphomas, and hairy cell leukemias. Immunotoxins described herein which are directed to CD74 are useful for inhibition and treatment of melanoma, neuroblastoma and myeloma cells.

The preferred cytotoxic reagents of this invention are at least 100 times, preferably at least 500 times and most preferably at least 1000 times more cytotoxic to target cells bearing a B cell marker than a comparison reagent comprised of the same antibody joined to EDN, a human non-toxic RNAse.

A. Antibodies to Cell Surface Markers

Antibodies refer to polypeptides substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

A variety of methods for producing monoclonal antibodies are known in the art. See, e.g., Goding, MONOCLONAL ANTIBODIES; PRINCIPLES AND PRACTICE, Academic Press, 2nd Edition (1986); and Harlow & Lane. A monoclonal antibody directed against or reactive with human B cells is obtained by using combinations of immunogens to immunize mice and screening hybridoma supernatant against cells which express the desired antigen or by a screening assay designed to be specific for monoclonal antibodies directed against the antigen of interest. Useful cell lines for screening for the antibodies of this invention are readily available or obtained. Such cells include the Burkitt's lymphoma cell lines Daudi, CA-46 and Raji.

CD22, a lineage-restricted B-cell antigen belonging to the Ig superfamily, is expressed on the surface of many types of malignant B cells, including but not limited to, acute lymphocytic leukemia (B-ALL), chronic B-lymphocytic cells (B-CLL), B lymphoma cells such as Burkitt's, AIDS-associated and Follicular lymphomas, and hairy cell leukemias, as well as on normal mature B lymphocytes. CD22 is not expressed in early stages of B-cell development, nor is it found on the surface of stem cells or terminal stage plasma cells. Vaickus, et al., *Crit. Rev. Oncol/Hematol.* 11:267–297 (1991). Additionally, no shed antigen is detected in normal human serum or serum from patients with CLL. Li, et al., *Cell. Immunol.* 118:85–99 (1989).

CD74, also known as the MHC Class II associated invariant chain (Ii), is found on B cells, macrophages, monocytes and other MHC Class II positive cells. In addition to the malignant B cells listed above, CD74 is also found on neuroblastoma, melanoma and myeloma cells.

Production of monoclonal antibodies directed against, e.g., B cells, is accomplished by: 1) immunization with human B cells followed by screening of the resultant hybridomas for reactivity against a non-human cell line transfected with human B cell antigens constructed in a manner similar to that described in Nishimura, et al., *Eur. J. Immunol.* 18:747 (1988) which is incorporated by reference herein; 2) immunization with a non-human cell line (preferably autologous to the animal to be immunized) transfected with human B cell antigens followed by screening of the resultant hybridomas for reactivity against a human B cell line; 3) immunization with human or non-human cell lines expressing human B cell antigens followed by screening of the resultant hybridomas for ability to block reactivity of existing anti-B cell monoclonal antibodies with a human B cell line; 4) immunization with human or non-human cell lines expressing human B cell antigens followed by screening of the resultant hybridomas for reactivity with purified native or recombinant B cell antigens; and 5) immunization with a recombinant derivative of human B cell antigens followed by screening of the resultant hybridomas for reactivity against a human B cell line. Upon review of this disclosure, those of skill will realize other methods of raising antibodies which can be used in this invention.

Recombinant DNA methodologies are used to synthesize the preferred antibodies of this invention. For example, a preferred antibody portion of an immunotoxin for use in humans is a "humanized" antibody against a B cell antigen which contains only murine complementarity-determining regions (CDRs) combined with human variable region frameworks and human constant regions.

Humanization techniques are well known in the art. See, for example, PCT Application Publication No. WO 87/02671; U.S. Pat. No. 4,816,567; EP Patent Application 0173494; Jones, et al., *Nature* 321:522 (1986); and Verhoeyen, et al., *Science* 239:1534 (1988). Manipulation of the CDR is a way of achieving humanized antibodies. See, for example, Jones, et al., *Nature* 321:522 (1988) and Riechmann, et al., *Nature* 332:323 (1988). For a review article concerning humanized antibodies see Winter & Milstein, *Nature* 349:293 (1991).

In addition to humanized, the antibody moieties of this invention are single chain antibodies. In one aspect of this invention, single chain antibodies are cloned from the parent hybridoma cell lines.

The Fv regions of monoclonal antibodies are cloned using the same general strategy. Typically, for example, poly(A)$^+$ RNA extracted from hybridoma cells is reverse transcribed using random hexamners as primers. The $V_H$ and $V_L$ domains are amplified separately by two polymerase chain reactions (PCR). Heavy chain sequences are amplified using 5' end primers which are designed according to the amino-terminal protein sequences of the heavy chains, and the 3' end primers according to consensus immunoglobulin constant region sequences (Kabat, et al., SEQUENCES OF PROTEINS OF IMMUNOLOGICAL INTEREST, 5TH ED., U.S. Department of Health and Human Services, Public Health Service, National Institutes of Health, Bethesda, Md. (1991). Light chain Fv regions are amplified using 5' end primers designed according to the amino-termainal protein sequences of the light chains and in combination with the primer C-kappa. One of skill in the art will recognize other suitable primers may be used.

The crude PCR products are subcloned into suitable cloning vectors which are well known to those of skill in the art and commercially available. Clones containing the correct size DNA insert are identified, for example, agarose gel electrophoresis. The nucleotide sequence of the heavy or light chain coding regions is then determined from double stranded plasmid DNA using the sequencing primers adjacent to the cloning site. Commercially available kits (e.g., the Sequenase® kit, United States Biochemical Corp., Cleveland, Ohio) are used to facilitate sequencing the DNA.

One of skill will appreciate that, utilizing the sequence information provided for the Fv regions, nucleic acids encoding these sequences are obtained using a number of methods well known to those of skill in the art. Thus, DNA encoding the Fv regions is prepared by any suitable method, including, for example, amplification techniques such as ligase chain reaction (LCR) (see Wu & Wallace, *Genomics*4:560 (1989), Landegren, et al., *Science*241:1077 (1988) and Barringer, et al., *Gene*89:117 (1990)), transcription amplification (see Kwoh, et al., *Proc. Nat'l Acad. Sci. USA*86:1173 (1989)), and self-sustained sequence replication (see Guatelli, et al., *Proc. Nat'l Acad. Sci. USA*87:1874 (1990)), cloning and restriction of appropriate sequences or direct chemical synthesis by methods such as the phosphotriester method of Narang, et al., *Meth. Enzymol.* 68:90 (1979); the phosphodiester method of Brown, et al., *Meth. Enzymol.* 68:109 (1979); the diethylphosphoramidite method of Beaucage, et al., *Tetra. Lett.* 22:1859 (1981); and the solid support method of U.S. Pat. No. 4,458,066.

The nucleic acid sequences which encode the single chain antibodies are identified by techniques well known in the art (see, Sambrook, et al.). Briefly, the DNA products described above are separated on an electrophoretic gel. The contents of the gel are transferred to a suitable membrane (e.g., Hybond-N®, Amersham) and hybridized to a suitable probe under stringent conditions. The probe should comprise a nucleic acid sequence of a fragment embedded within the desired sequence.

If the DNA sequence is synthesized chemically, a single stranded oligonucleotide will result. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are later ligated together.

Alternatively, subsequences may be cloned and the appropriate subsequences cleaved using appropriate restriction enzymes. The fragments may then be ligated to produce the desired DNA sequence.

Once the Fv variable light and heavy chain DNA is obtained, the sequences may be ligated together, either directly or through a DNA sequence encoding a peptide linker, using techniques well known to those of skill in the art. Thus, the entire sequence encodes the Fv domain in the form of a single chain antibody.

Alternatively, antibodies directed against B cells, for example, are commercially available from suppliers of immunological reagents (for example, Ancell Corp., Bayport, MN (RFB4); Becton Dickinson, San Jose, Calif.; The Binding Site, Inc., San Diego, Calif.; CalTag Laboratories, South San Francisco, Calif.; Boehringer Mannheim Biochemicals, Indianapolis, Ind.; Pharmacia Biotech, Piscataway, N.J.: and Zymed, Foster City, Calif.). RFB4 is a preferred antibody of this invention which has surprising efficacy when compared to other antibodies. It has been characterized and is described in a PCT Patent Application, filed Mar. 19, 1998, entitled FitzGerald, et al., "Recombinant RFB4 Immunotoxins Exhibit Potent Cytotoxic Activity for CD-22 Bearing Cells and Tumors" as well as in Mansfield, el al., *Bioconj. Chem.* 7:557 (1996); Mansfield, et al., *Biochem. Soc. Trans.* 25:709 (1997); and Mansfield, et al., *Blood*90:2020 (1997); all of which are incorporated in this disclosure in their entirety.

B. Cytotoxic Onc Protein

This application discloses a new use for the onc protein from *Rana pipiens*. The *Rana pipiens* onc protein is a substantially pure protein derived from the eggs and/or embryos of *Rana pipiens* having a molecular weight of about 12,000 Daltons by mass spectrometry, and an isoelectric point of between 9.5 and 10.5. It is also exemplified by a product sometimes referred to herein by the trade name ONCONASE®, available from Alfacell Corporation, Bloomfield, N.J.

Preferably for this invention, the onc proteins are proteins having the amino acid sequence set out in SEQ ID NO:1.

The onc protein used in this invention is unique compared to other RNases used in immunotoxin construction because it is a monomeric member of the pancreatic RNase family and is toxic to certain cancer cells without an internalizing ligand (see U.S. Pat. No. 5,559,212). However, it is a discovery of this invention that, when conjugated to an antibody directed to a B cell, the cytotoxicity of the onc protein dramatically increases up to as much as 2,000 fold. In spite of the cytotoxicity to cancer cells, patient toxicity and immunogenicity arc expected to be low because of the efficiency of this particular immunotoxin and the small size of the toxin.

It will be understood by those of skill in the art that SEQ ID NO:1 may be altered in a manner that does not substantially affect the functional advantages of the sequence provided here. For example, glycine and alanine are typically considered to be interchangeable as are aspartic acid and glutamic acid and asparagine and glutamine. Any such modification in which the functional advantages of the sequence are maintained are intended to be covered by the sequence described in SEQ ID NO:1.

An exemplary recombinant onc protein described and claimed herein is defined as comprising SEQ ID NO:2. The recombinant onc proteins of this invention have similar measurable ribonuclcolytic activity compared to native onc protein. However, one of skill in the art will recognize that many different variations of one sequences will encode onc proteins with roughly the same measurable ribonucleolytic activity as native onc protein.

For a description of preferred recombinant onc proteins, variants of recombinant onc proteins, and techniques for synthesizing recombinant onc proteins, see PCT Application No: PCT/US97/02588 which is incorporated by reference herein.

C. Immunotoxins

The toxic moiety and the antibody may be conjugated by chemical or by recombinant means (see, Rybak, et al., *Tumor Targeting*1:141 (1995)). Chemical modifications include, for example, derivitization for the purpose of linking the moieties to each other, either directly or through a linking compound, by methods that are well known in the art of protein chemistry. In the presently preferred chemical conjugation embodiment, the means of linking the toxic moiety and the recognition moiety comprises a heterobifunctional coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteincs in each moiety which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages. The means of linking moieties of the immunotoxins may also comprise a peptidyl bond formed between moieties which are separately synthesized by standard peptide synthesis chemistry or recombinant means.

Possible chemical modifications of the protein moieties of the present invention also include derivitization with polyethylene glycol (PEG) to extend time of residence in the circulatory system and reduce immunogenicity, according to well known methods (See for example, Lisi, et al., *Applied Biochein.* 4:19 (1982); Beauchamp, et al., *Anal. Biochem.* 131:25 (1982); and Goodson, et al., *Bio/Technology*8:343 (1990)).

Possible genetic engineering modifications of the proteins of the immunotoxins include combination of the relevant functional domains of each into a single chain multi-functional biosynthetic protein expressed from a single gene derived by recombinant DNA techniques. (See, for example, PCT published application WO/88/09344). Furthermore, recombinant DNA techniques can be used to link the recombinant onc protein and the antibody. Accordingly, the immunotoxin can comprise a fused protein beginning at one end with the onc protein and ending with the antibody.

Methods of producing recombinant fusion proteins are well known to those of skill in the art. Thus, for example, Chaudhary, et al., *Nature*339:394 (1989); Batra, et al., *J. Biol. Cliem.* 265:15198 (1990); Batra, et al., *Proc. Nat'l Acad. Sci. USA*86:8545 (1989); Chaudhary, et al., *Proc. Nat'l Acad. Sci. USA*87:1066 (1990), all incorporated by reference, describe the preparation of various single chain antibody-toxin fusion proteins.

In general, producing immunotoxin fusion proteins involves separately preparing the Fv light and heavy chains and DNA encoding the onc protein to be used. The two sequences are combined in a plasmid or other vector to form a construct encoding the particular desired fusion protein. A simpler approach involves inserting the DNA encoding the particular Fv region into a construct already encoding the desired onc protein.

Thus, for example, DNA encoding anti-B cell single chain antibody/onc protein immunotoxins is most easily prepared by inserting the DNA encoding the antibody $V_H$ and $V_L$ chains (Fv region) into constructs already containing DNA encoding the desired onc protein or vice versa. The DNA sequence encoding the Fv region is inserted into the construct using techniques well known to those of skill in the art.

Mammalian cells have been used to express and secrete hybrid molecules such as antibody-cytokines (Hoogenboom, et al., *Biochem. Biophys. Acta*1096:345 (1991); Hoogenboom, et al., *Mol. Immunol.* 28:1027 (1991)) and antibody-enzyme (Casadei, et al., *Proc. Nat'l Acad. Sci. USA*87:2047 (1990); Williams, et al., *Gene*43:319 (1986)). In part, immunogenicity of foreign proteins is due to incorrect glycosylation patterns present on recombinant proteins. Therefore, eukaryotic cell lines are preferred over prokaryotic cells as the expressed proteins are glycosylated. Human derived cell lines are particularly preferred in that these cells incorporate a sialic acid as the terminal glycoside. Cell lines such as the hamster CHO and BHK, as well as the HEK-293 human fibroblast line have been used to express recombinant human proteins.

Other genetic engineering modifications of the protein moieties of the immunotoxins of this invention include deletions of functionally unnecessary domains to reduce the size of the protein or to modify other parameters which facilitate production or utility, such as sequence changes to affect the solubility (e.g., cysteine to serine) or glycosylation sites. One skilled in the art would appreciate that many additional well known chemical and genetic modifications of proteins may be advantageously applied to any protein which, like the present cytotoxic reagent, is intended for parenteral administration.

Preferred immunotoxins of the present invention arc fusion proteins containing as the toxic moiety a protein having the amino acid sequence of SEQ ID NO:1 and a humanized antibody that binds a specific cell surface marker on the cell of interest (more preferably against B cells). The construction of this unique genetic linkage of the fusion protein between the onc protein and the antibody eliminates the heterogeneity of chemically linked antibody/onc protein conjugates. This, it is believed, may contribute to the increased potency and decreased immunogenicity of the immunotoxin.

The invention includes nucleic acid constructs that encode the novel proteins described here. A nucleic acid construct is one which, when incorporated into an appropriate vector, is capable of replicating in a host. The constructs may be linked to other sequences capable of affecting the expression of the construct, such as promoters and enhancers.

The immunotoxin of the present invention may be utilized for the selective killing of tumor cells. This method is based on the appropriate selection of an antibody that binds to cell surface markers found specifically or predominantly on the type of cell that is to be selectively killed. For example, the immunotoxin of this invention includes those comprising an antibody that binds to a tumor cell-specific surface marker, of which many are known in the art. In the preferred embodiment for a human application, the antibody is a humanized single chain protein, or a modified form thereof, which preferentially binds B-cells, indicating malignancy.

D. Pharmaceutical Compositions

The present invention also relates to a pharmaceutical composition comprising immunotoxins of the present invention in a pharmaceutically acceptable carrier. In therapeutic applications, compositions are administered to a patient suffering from a disease, in an amount sufficient to cure or at least partially arrest the disease and its complications. An amount adequate to accomplish this is defined as a therapeutically effective dose. Amounts effective for this use will depend on the severity of the disease and the general state of the patient's health.

Advantageously, the pharmaceutical composition is suitable for parenteral administration. The immunotoxins of the present invention may be administered by various means appropriate for different purposes, for example, for treating tumors in various parts of the body, according to methods known in the art for other immunotoxins. (See, for example, Rybak, et al., Human Cancer Immunology, in IMMUNOLOGY AND ALLERGY CLINICS OF AMERICA, W. B. Saunders, 1990, and references cited therein). Accordingly, the present invention also relates to pharmaceutical compositions comprising an immunotoxin of this invention and a pharmaceutically acceptable carrier, particularly such compositions which are suitable for the above means of administration.

Single or multiple administrations of the compositions may be administered depending on the dosage and frequency as required and tolerated by the patient. In any event, the composition should provide a sufficient quantity of the proteins of this invention to effectively treat the patient.

Preferably, the compositions for administration will commonly comprise a solution of the fusion protein comprising the single chain antibody and the onc protein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.01 to 100 mg per patient per day. Dosages from 0.1 up to about 1000 mg per patient per day may be used, particularly when the drug is administered to a secluded site and not into the blood stream, such as into a tumor or an organ within which a tumor resides. Actual methods for preparing parenterally administrable compositions will be known or apparent to those skilled in the art and are described in more detail in such publications as REMINGTON'S PHARMACEUTICAL SCIENCE, 15TH ED., Mack Publishing Co., Easton, Pa., (1980).

Further, the present invention relates to a method of selectively killing cells using a selective immunotoxin of the present invention having an antibody specific for a target on the surface of the cells to be killed under conditions allowing binding of the antibody. Binding of the antibody to the surface marker on a cell causes the onc protein of the reagent to selectively kill the cell. This method of the present invention may be used for cell separation in vitro by selectively killing unwanted types of cells, for example, in bone marrow prior to transplantation into a patient undergoing marrow ablation by radiation.

EXAMPLES

In the following non-limiting examples, the present invention is exemplified by a immunotoxin in which the toxic moiety is ONCONASE® and the antibodies recognize tumor cells, in particular, B cells.

Example 1

Production of Native and Recombinant Onc Protein from *Rana pipiens*

A. Isolation and Purification of Native Onc Protein

Techniques describing the isolation of oocytes from *Rana pipiens*, in vitro fertilization of the eggs, and the isolation and purification of native onc protein from frog embryos are exquisitely detailed in U.S. Pat. Nos. 5,559,212 and 5,728,805, which are both incorporated by reference herein.

B. Production and Assaying of Recombinant Onc Protein

The production of recombinant onc protein was done as described in PCT application PCT/US97/02588. Ribonucleolytic activity using high molecular weight RNA and tRNA was determined following published protocols, Newton, et al., *J. Neurosci.* 14:538 (1994) at 37° C. through the formation of perchloric acid soluble nucleotides (see, Newton, et al., *Biochem.* 35:545 (1996)). With poly (A,C), UpG, and poly U, ribonuclease activity was assayed spectrophotometrically according to Libonati, et al., *Biochim. et Biophys.* *Acta* 788:356 (1984), and Libonati & Floridi, *Eur. J Biochem.* 8:81 (1969). Briefly, activity was assayed by measuring the increase in absorbance at 260 nm. Incubation mixtures (1 mL of 10 mM imidazole, 0.1 M NaCl, pH 6.5 or pH 7) contained substrate and appropriate amounts of enzyme solution at 25° C. The in vitro translation assay (St. Clair, et al., *Proc. Nat 'l Acad. Sci. USA* 84:8330 (1987)), and the cell viability assays (Pearson, et al., *J. Nat'l Cancer Inst.* 83:1386 (1991)), using the MTT method of Mossman were performed as previously described.

Example 2

Chemical Analysis and Composition of Onc Proteins

The native onc protein described above has been well characterized chemically. To be as fully functional as the native on protein, it is believed the recombinant onc protein should have the chemistry and structure as described below.

The native onc protein was purified to homogeneity (as established by standard tests used to assay the homogeneity of proteins). By electrophoresis, the molecular weight of the native onc protein was determined to be approximately 14,500 Daltons. Calculation of the molecular weight based upon the listed amino acid sequence (see, infra), indicated the molecular weight of native onc protein should be 11,860 Daltons. However, because metal ions may have bonded to the protein despite all efforts to remove them, and because different isotopes may be involved, the molecular weight of the native onc protein was 12,430 Daltons as determined by mass spectroscopy. In view of this discrepancy, the molecular weight of the pharmaceutical as determined by mass spectrometry was considered to be approximately 12,000 Daltons. The isoelectric point (pI) of native onc protein was found to be between about 9.5 and 10.5, as determined by isoelectric focussing. The amino terminal group of native onc protein was blocked and was found to be essentially free of carbohydrates (as determined by anthrone and orcinol methods).

Table 1 indicates the amino acid composition of the native onc protein.

TABLE 1

Amino Acid Analysis of Native Onc Protein

| AMINO ACID RESIDUE | % MOL (24 HOUR ACID HYDROLYSIS) |
|---|---|
| Aspartic acid/Asparagine | 13.99 |
| Threonine | 9.30 (Note 1) |
| Serine | 7.78 |
| Glutamic acid/Glutamine | 6.10 |
| Proline | 4.36 |
| Glycine | 3.09 |
| Alanine | 3.09 |
| Cysteine/2 | 6.92 (Note 1) |
| Valine | 8.20 |
| Methionine | 0.85 (Note 1) |
| Isoleucine | 4.86 (Note 2) |
| Leucine | 5.22 |
| Tyrosine | 2.96 |
| Phenylalanine | 6.05 |
| Histidine | 2.88 |
| Lysine | 11.62 |
| Arginine | 2.70 |

TABLE 1-continued

Amino Acid Analysis of Native Onc Protein

| AMINO ACID RESIDUE | % MOL (24 HOUR ACID HYDROLYSIS) |
|---|---|
| Tryptophan | Not Determined (Note 3) |
| Approximate Total | 99.97% |

Note 1: Threonine, cysteine/2 and methionine are partially destroyed during hydrolysis and this value is uncorrected for such partial destruction.
Note 2: This value is uncorrected for incomplete hydrolysis.
Note 3: Tryptophan cannot be detected in acid hydrolysis of proteins because it is destroyed and is consequently shown as Not Determined. However, analysis of the ultraviolet spectrum revealed the presence of one tryptophan residue per molecule.

TABLE 2

Amino Acid Composition (as calculated from amino acid sequence)

| AMINO ACID | APPROX. # OF RESIDUES (PER MOLECULE OF NATIVE ONC PROTEIN) |
|---|---|
| Aspartic acid | 6 |
| Asparagine | 8 |
| Threonine | 10 |
| Serine | 8 |
| Glutamic acid | 3 |
| Pyroglutamic acid | 1 |
| Glutamine | 2 |
| Proline | 4 |
| Glycine | 3 |
| Alanine | 3 |
| Cysteine/2 | 8 |
| Valine | 8 |
| Methionine | 1 |
| Isoleucine | 6 |
| Leucine | 5 |
| Tyrosine | 3 |
| Phenylalanine | 6 |
| Histidine | 3 |
| Lysine | 12 |
| Arginine | 3 |
| Tryptophan | 1 |
| Approximate Total | 104 |

The native onc protein has been sequenced. The N-terminus of the native protein is pyroglutamic acid (<Glu). This is a cyclized derivative of glutamic acid which is devoid of the free amino group necessary for direct sequencing and which therefore "blocks" the N-terminus of the protein. The amino terminus of the molecule has been altered to facilitate recombinant production of the molecule as set out in previously cited PCT/US97/02588. The prefened amino acid sequence of the cytotoxic RNase is shown as SEQ ID NO:1.

Example 3

ANTI-CD22-ONCONASE® IMMUNOTOXIN

A. MATERIALS AND METHODS

ONCONASE® (previously named P-30) was provided by Alfacell Corp. as a lyophilized protein and was dissolved in phosphate buffered saline (PBS). Stock solutions of at least 1 mg/mL were kept frozen at −20° C. until dilutions were prepared for assays. All other reagents were purchased from sources previously described (Rybak, et al., *J. Biol. Chem.* 266:21202 (1991); Newton, et al., *J. Biol. Chem.* 267:19572 (1992); Mikulski, et al., *Cell Tissue Kinet.* 23:237 (1990)), herein incorporated by reference.

LL2 is a murine monoclonal antibody that recognizes and specifically binds to CD22 on human B cells. The LL2 antibody was provided by Immunomedics, Inc. (Morris Plains, N.J.). RFB4 is also a murine monoclonal antibody that binds to CD22. This antibody is available from many sources, including Ancell Corp.

Three Burkitt lymphoma cell lines (Daudi (ATCC CCL 213), CA 46 (ATCC CRL 1648), and Raji (ATCC CCL86)) were grown in RPMI 1640 media containing 10% fetal calf serum (FCS), 2 mM glutamine, 1 mM sodium pyruvate, and 10 µg/mL gentamicin. HUT 102, a human cutaneous T cell lymphoma cell line (ATCC TIB 162) was also grown in supplemented RPMI medium. All cells were incubated at 37° C. in a 5% $CO_2$ humidified atmosphere.

B. PREPARATION OF LL2-ONCONASE® IMMUNO-TOXINS

Disulfide linked conjugates were prepared as described in Newton, et al., *J. Biol. Chem.*, 267:19572 (1992), with the following modifications. Antibody (12.5 nmol) was incubated with 250 nmol 2-iminothiolane and 2.5 mM 5,5'dithiobis(2-nitrobenzoic acid) (DTNB) in 100 mM sodium borate, pH 8.5, at room temperature for 1 hour in a final volume ≦0.5 mL. The reaction mixture was applied to a PD-10® column (Pharmacia Biotech, Piscataway, N.J.) equilibrated with Buffer A (0.1M $NaPO_4$, pH 7.5, containing 0.1 M NaCl).

SPDP-modified ONCONASE® (0.9-1.2 mol N-succinimidyl 3 (2-pyridyldithio) propionate (SPDP)/mol ONCONASE® was prepared as described (Newton, et al., (1992) supra). The SPDP-modified ONCONASE® (340 nM) was reduced for 1 hour at room temperature with dithiothreitol (DTT) at a final DTT concentration of 2 mM and gel filtered on a PD- 10® column equilibrated with Buffer A to remove excess DTT. The modified ONCONASE® was added to the modified antibody and the reaction incubated overnight at room temperature. The ONCONASE® was at least a 10-fold molar excess over the antibody.

Thioether-linked conjugates were prepared according to Rybak, et al., *Drug Delivery* 1:3 (1993) and Newton, et al., *Int'l J. Oncology* 8:1095 (1996) using m-maleimidobenzoyl-N-hydroxysuccinimide ester (MBS). Briefly, LL2 antibody (2 mg) was incubated with a 5-fold molar excess of MBS (stock solution, 30 mM in DMF) for 10 min at room temperature. The reaction contents were applied to a PD-10® column equilibrated with Buffer A. Peak fractions (1.5 mL) were pooled. The SPDP-modified ONCONASE® was dialyzed against 0.1 M sodium acetate, pH 4.5, containing 0.1 M NaCl, followed by incubation with 25 mM DTT (final concentration) for 30 min at room temperature. The reaction contents were applied to a PD-10® column equilibrated with Buffer A and the peak fractions pooled and added to the MBS antibody. The reaction was incubated at room temperature overnight. The ONCONASE® was present in a ≧ 10 fold molar excess over antibody. The conjugates were separated from unreacted ONCONASE® by gel filtration on a TSK-3000® HPLC column (Toso-Haas).

The amount of protein present in the preparations was determined by UV spectroscopy following Beer's Law: [A=ε(conc.)] with the following extinction coefficients at 277 nm: ONCONASE®, ε(1%)=7.3; and immunotoxins, ε(1%)=10.

The moles of ONCONASE® conjugated to antibody was determined by gel electrophoresis of the reduced immunotoxins along with standards of ONCONASE® and antibody. The gel was analyzed using Image (NIH public domain software).

Analysis of ONCONASE® immunotoxins by SDS polyacrylamide gel electrophoresis under reducing conditions demonstrated the component proteins were regenerated after reduction. Under non-reducing conditions, the antibody conjugates consisted of multiple high molecular weight forms. The reactivity of the cross-linker groups in the thiol-disulfide interchange reaction may explain the heterogeneity of the conjugate. The immunotoxins contained 1-2 moles of ONCONASE®/mol of antibody. The purified immunotoxins did not, by gel electrophoresis, appear to contain significant amounts of free antibody, presumably because the ≧10 fold molar excess of ONCONASE® yielded essentially all immunotoxin and no free antibody.

C. PREPARATION OF RFB4-ONCONASE® IMMUNOTOXINS

RFB4-ONCONASE® immunotoxins are prepared as described above. Because RFB4 recognizes CD22, immunotoxins which contain RFB4 are also cytotoxic to malignant B cells. Thus, the experiments described below can be performed with RFB4-ONCONASE® as well.

Example 4

IN VITRO CELL VIABILITY STUDIES

Protein synthesis was measured as described in Rybak, et al., *J Biol. Chem.* 266:21202 (1991). The same protocol was used to measure RNA synthesis, except the cells were pulsed with 3 µCi of [$^3$H]uridine. Cell number was determined by a direct count with a hemocytometer. An aliquot of cells was incubated for 5 min with an equal volume of 0.5% Trypan Blue exclusion dye and viable cells were scored. The MTT colorimetric assay (Mossman, T., *J. Immunol. Methods* 65:55 (1983)) was performed as described (Mikulski, et al., *Cell Tissue Kinet.* 23:237 (1990)).

The IC$_{50}$ for protein synthesis inhibition in Burkitt lymphoma cells by ONCONASE®-immunotoxins is presented in Table 4.

TABLE 4

Protein Synthesis Inhibition by ONCONASE®-Immunotoxins

| | IC$_{50}$ | |
|---|---|---|
| Cell Line | ONCONASE® | LL2-ONCONASE® |
| Daudi | >200 nM | 100 pM |
| CA 46 | >200 nM | 800 pM |
| Raji | >200 nM | 800 pM |
| HUT 102 | 30 nM | >100 nM |

The concentrations of immunotoxin required to inhibit protein synthesis 50% in B cells after 24 hours are in the picomolar range compared to the nanomolar range for unconjugated ONCONASE®. HUT 102 cells, which do not express CD22, were not sensitive to the LL2-ONCONASE® immunotoxin but were more sensitive to the unconjugated ONCONASE® than the B-cell lines. See FIG. 1.

Figure 2:
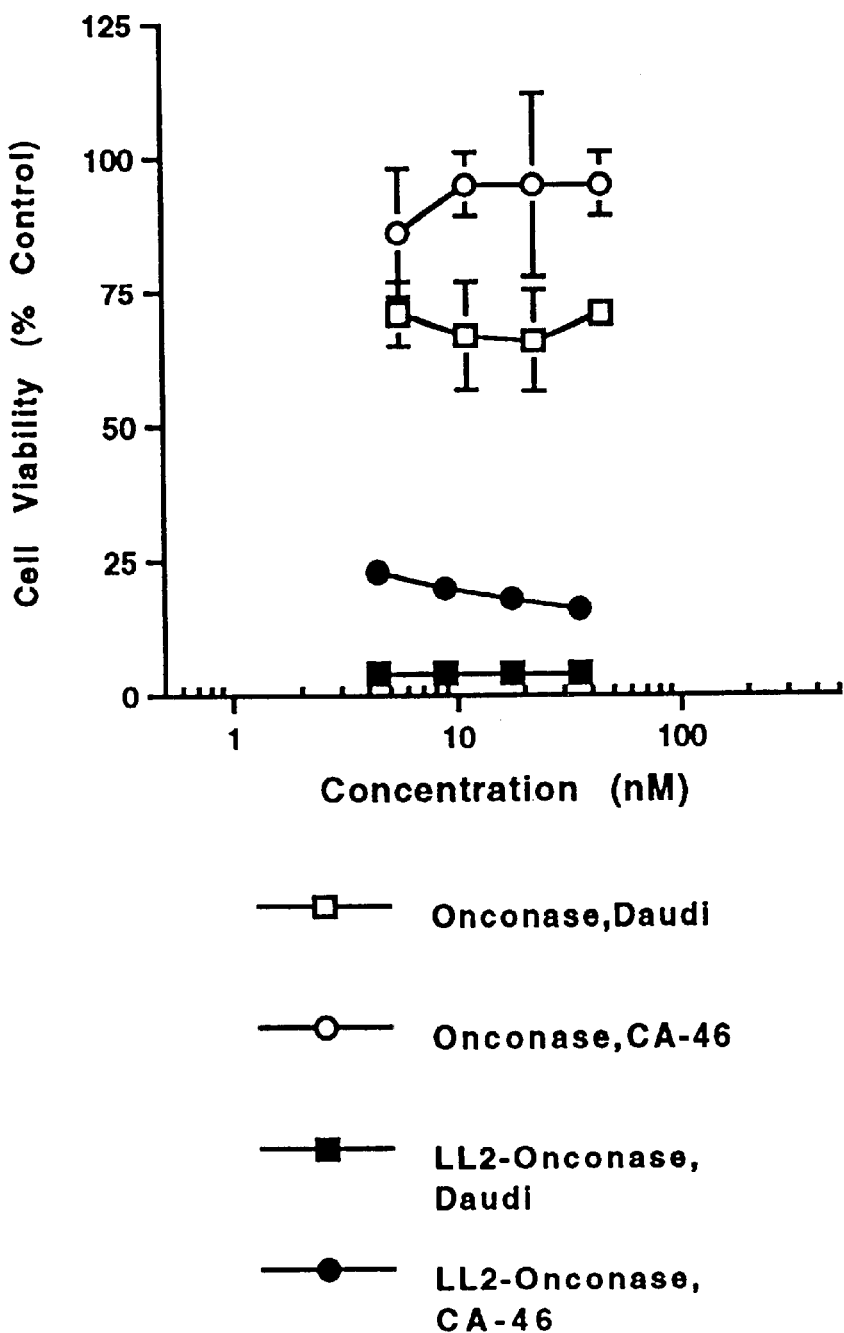
FIG. 2 demonstrates the superior cytotoxicity of LL2-ONCONASE® to Burkitt Lymphoma cell lines when compared to ONCONASE® alone.

As can be seen in FIG. 2, ONCONASE(G) alone was not cytotoxic to B-lymphoma cells after 24 h compared to ONCONASE® conjugated to the LL2 antibody. Thus, ONCONASE® conjugated to antibodies capable of internalization was more potent than the unconjugated ONCONASE®.

Figure 3:
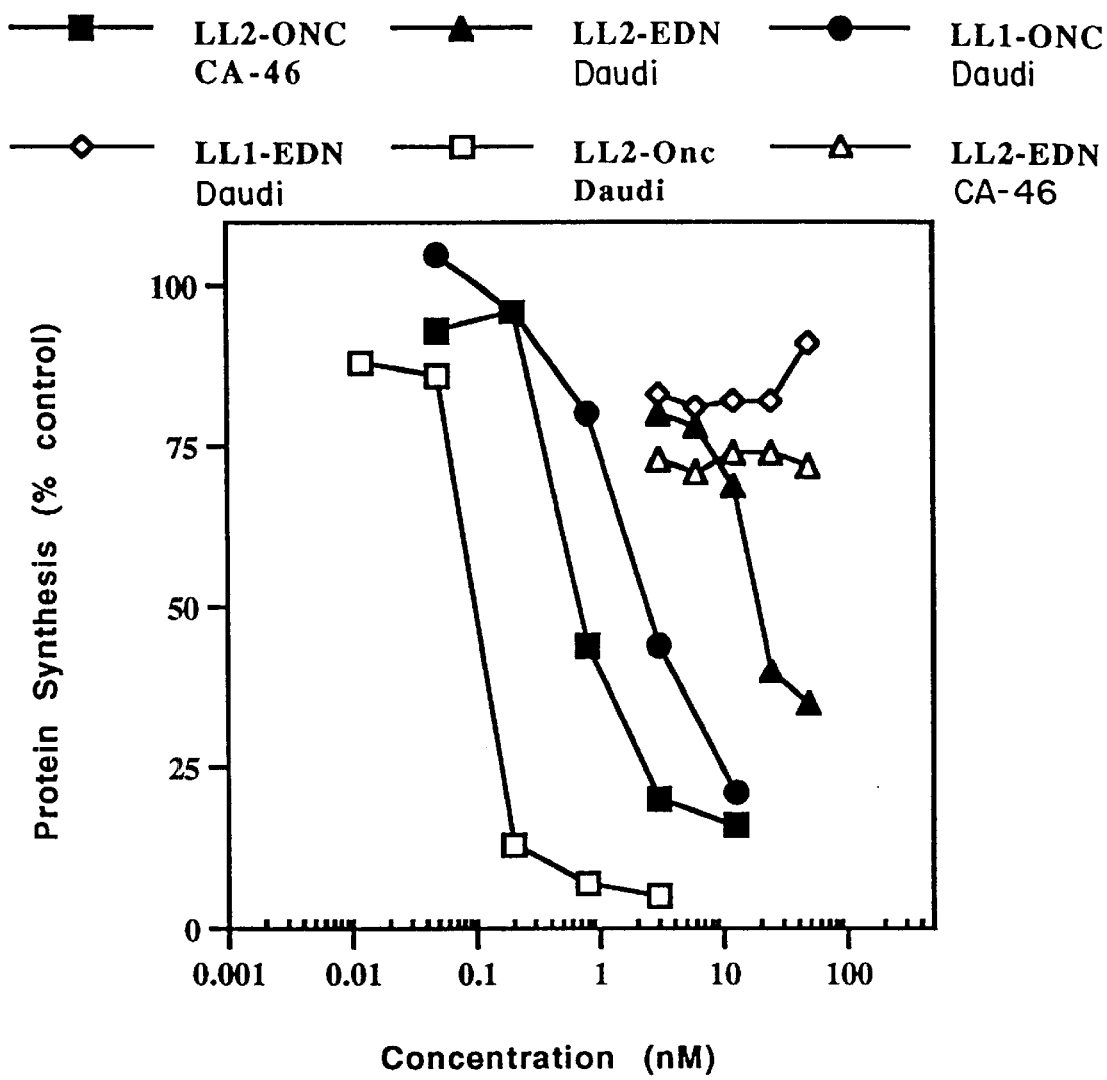
FIG. 3 indicates that ONCONASE® conjugated to antibodies directed against CD22 is more inhibitory of protein synthesis than EDN conjugated to anti-CD22 antibodies. EDN is a human non-toxic RNase as described in the text.
Figure 4:
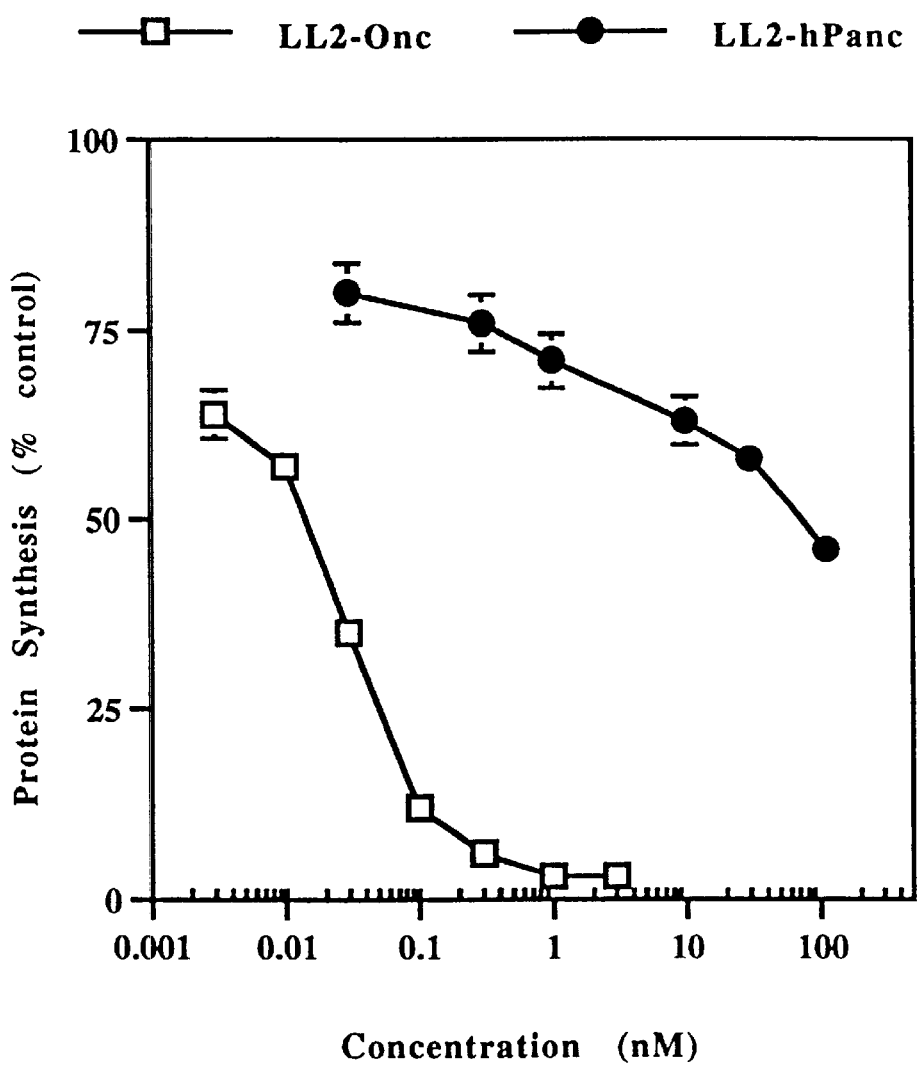
FIG. 4 indicates that ONCONASE® is more inhibitory of protein synthesis when conjugated to antibodies compared to human pancreatic RNase.
Figure 5B:
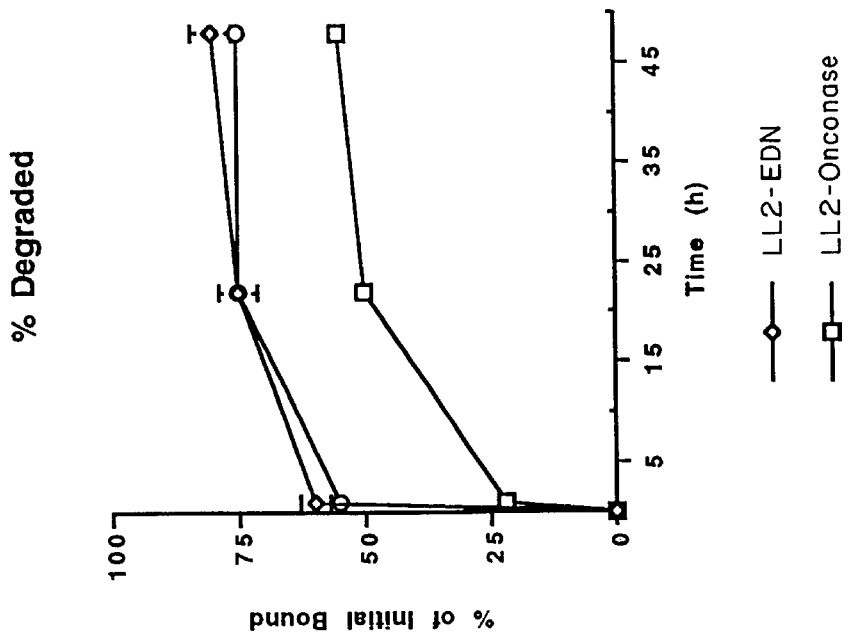
FIGS. 5A and 5B demonstrate that $^{125}$-I labeled LL2-ONCONASE® is not degraded by the lysosomes of Daudi cells as rapidly as the LL2 antibody or the LL2-EDN immunotoxin.
Figure 5A:
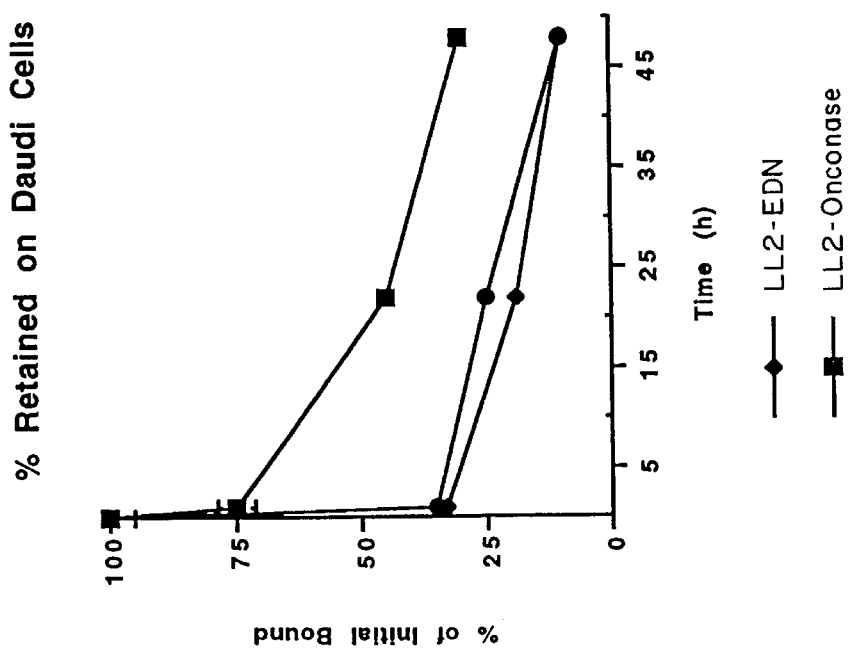
Figure 6:
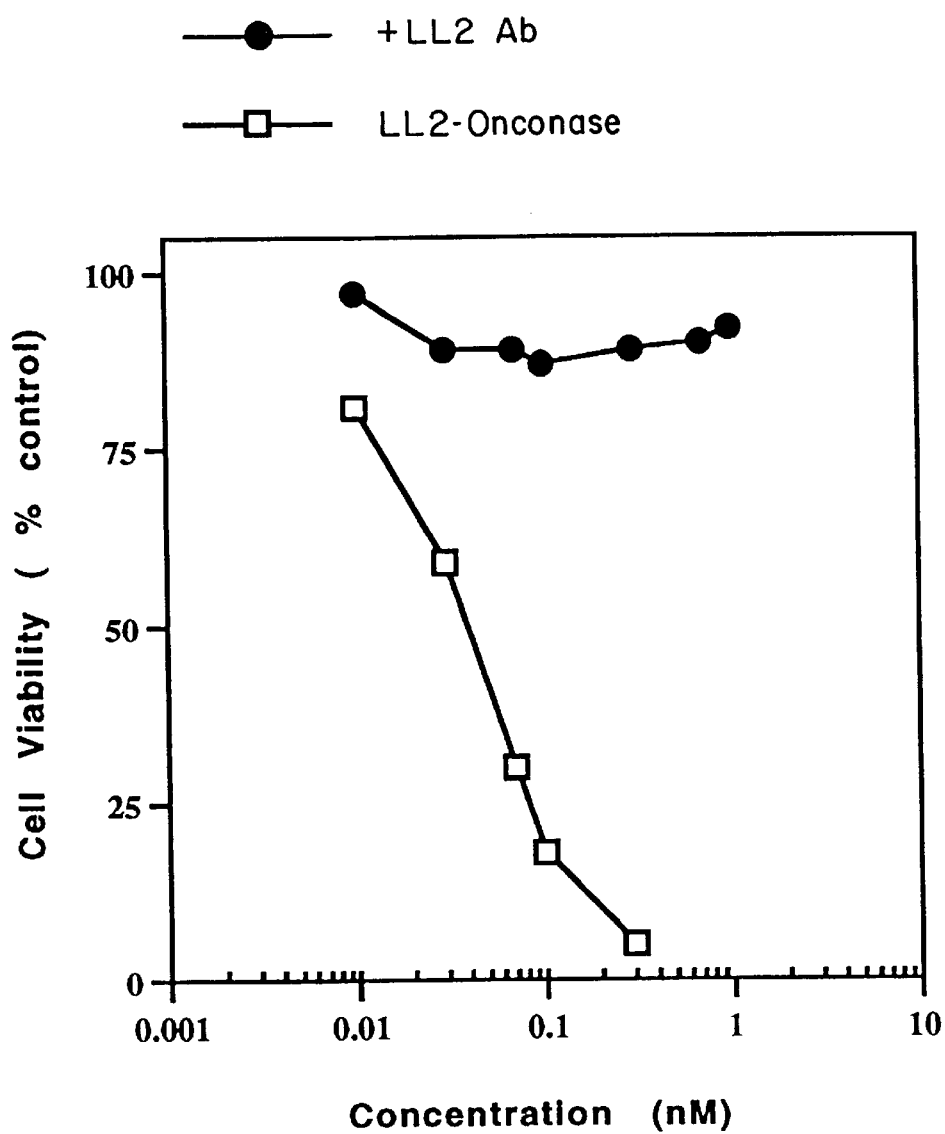
FIG. 6 demonstrates that LL2 antibody diminishes the cytotoxic effect of LL2-ONCONASE®. It is believed that LL2 competes for binding to CD22 with LL2-ONCONASE® and prevents the internalization of the ONCONASE®, thus reducing cytotoxicity.

In addition to being more effective than ONCONASE® alone, FIGS. 3 and 4 demonstrate the ONCONASE® immunotoxins were much more effective than immunotoxins in which the toxic moiety was either a human non-toxic RNase, eosinophil-derived neurotoxin (EDN) (FIG. 5) or a human pancreatic RNase (FIG. 6).

In FIG. 5, LL2 or LL1 antibodies were conjugated to EDN as described above and assayed on Daudi or CA 46 Burkitt s lymphoma cells. []It is believed that LL1 and LL2 immunotoxins are delivered to the lysosomes where the immunotoxin is degraded to the antibody and RNase moieties. The RNase leaves the lysosome and enters the cytosol where it interferes with ribosomal activity. From the data shown in FIG. 5, it is postulated that ONCONASE® is about 2,000 fold more active than EDN because ONCONASE® is not inactivated by degradation by the lysosome. Therefore, the protein that enters the cytosol is an intact cytotoxin.

In FIG. 6, LL2-ONCONASE® was compared to LL2-pancreatic RNase. Again, at concentrations of about 1 nM, LL2-ONCONASE® completely blocked protein synthesis. At the same concentration, only about 75% of protein synthesis had been blocked by the addition of LL2-pancreatic RNase.

Figure 7:
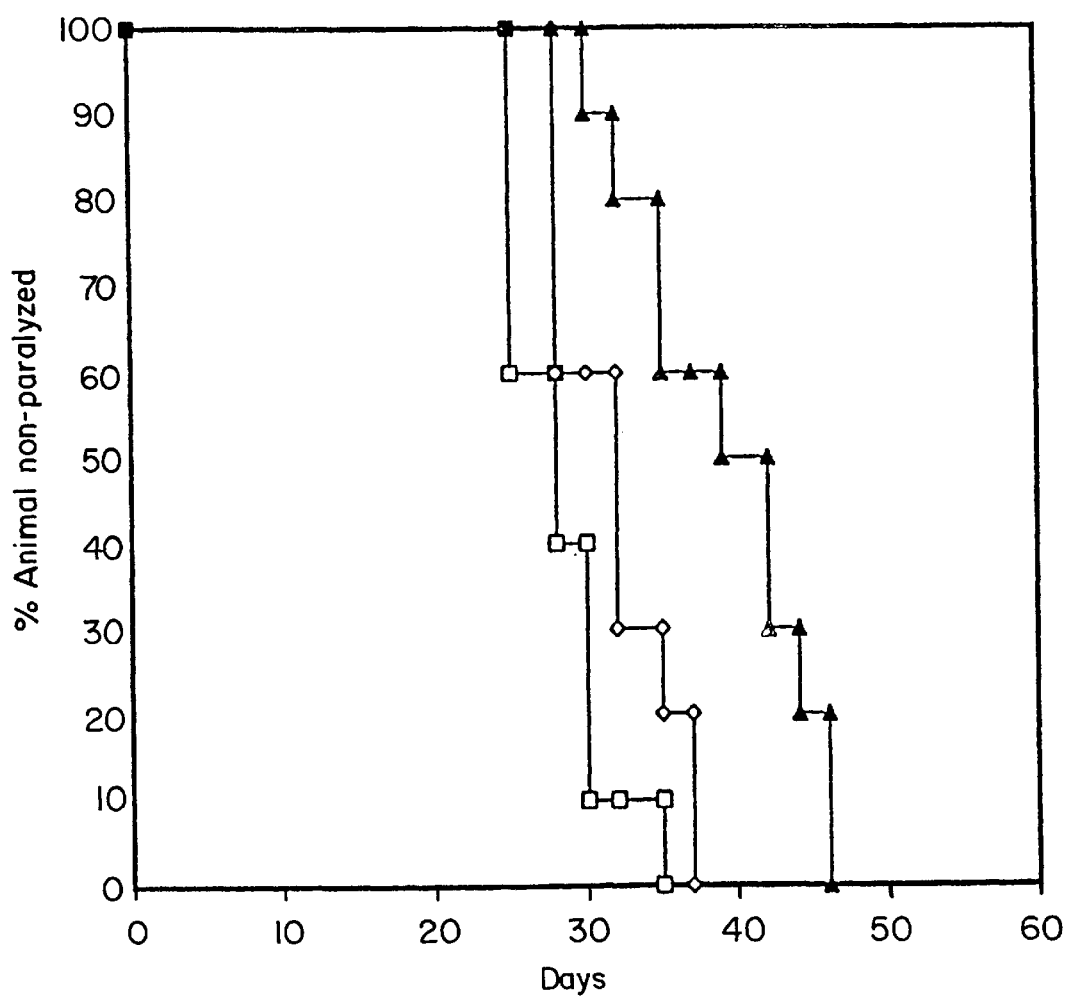
FIG. 7 is a survival graph showing LL2-ONCONASE® protected SCID mice from B cell lymphoma. $5 \times 10^6$ Daudi cells were implanted intraperitoneally in mice. 24 hours later, the mice were treated intravenously with 500 μg of the indicated compound.

To test the hypothesis that ONCONASE® was not degraded by the lysosomes leading to increased inhibition of protein synthesis and cytotoxicity, $^{125}$-I labeled LL2 and LL2 immunotoxins were added to Daudi cells. As can be seen in FIG. 7, after the indicated time span, cells treated with LL2-ONCONASE® contained more $^{125}$-I labeled protein in their lysates, indicating the immunotoxin was degraded at a slower rate than LL2-EDN and LL2 alone. Thus, it would appear that ONCONASE® is not degraded in the lysosomes.

To test the hypothesis that CD22 mediates the toxicity of ONCONASE® immunotoxins via binding of the antibody portion of the hybrid protein, the immunotoxins were assayed in the presence of excess LL2 antibody (FIG. 6). The cytotoxicity observed in Daudi cells after 24 h in the presence of the ONCONASE® immunotoxins was reversed by an equimolar amount of LL2. These data show that CD22 can mediate ONCONASE® cytotoxicity to Burkitt lymphoma cells.

Example 5

IN VIVO EFFICACY OF LL2-ONCONASE® IMMUNOTOXINS

To test the effect of LL2-ONCONASE® in vivo, Daudi cells were implanted into SCID mice. One day later, the mice were treated with ONCONASE® and LL2-ONCONASE®, LL2-Pseudomnas exotoxin and LL2-doxorubicin immunotoxins.

As can be seen in Table 5, LL2-ONCONASE® did not cause cytotoxic side effects (death) in mice. As a comparison, the mice were treated as well with LL2 conjugated to a mutant of domain II of Pseudomonas exotoxin. As can be seen, this immunotoxin was lethal. Thus, it appears that ONCONASE® as the toxic moiety of an immunotoxin is not toxic to the treated animal and therefore would be tolerated better as a therapeutic.

TABLE 5

In vivo Cytotoxicity of LL2-ONCONASE Immunotoxins

| | Toxicity in Mice | |
|---|---|---|
| Dose Schedule | Total Dose (µg) | Death/Total |
| LL2-PE38KDEL* | | |
| 80 µg i.p. × 1 | 80 | 2/2 |
| 35 µg i.p. QD × 4 | 140 | 2/2 |

TABLE 5-continued

In vivo Cytotoxicity of LL2-ONCONASE Immunotoxins

| | | Toxicity in Mice |
|---|---|---|
| Dose Schedule | Total Dose (μg) | Death/Total |
| LL2-ONCONASE | | |
| 100 μg i.p × 1 | 100 | 0/3 |
| 100 μg i.p. QOD × 5 | 500 | 0/3 |
| 100 μg i.p. QD × 5 | 500 | 0/3 |
| 500 μg i.p. × 1 | 500 | 0/3 |

*Kreitman, et al., Cancer Res. 53:819 (1993)
QD = daily
QOD = every other day

Table 6 shows the effects of LL2-ONCONASE® and LL2-doxorubicin on Daudi-implanted SCID mice. The mice were implanted with 5×10⁶ Daudi cells intravenously. 24 hours later, treatment began with 5 equal doses daily. The doxorubicin immunotoxin was injected intravenously and the ONCONASE® immunotoxin was injected intraperitoneally. As can be seen, by weight, almost one half the amount of LL2-ONCONASE® significantly enhanced the survival of the mice compared to the doxorubicin, a systemic chemotherapeutic reagent.

TABLE 6

Treatment in SCID Mice with Disseminated Daudi Lymphoma

| Immunotoxin | Total Dose | % of Mice with Enhanced Survival Relative to Antibody Alone |
|---|---|---|
| LL2-doxorubicin | 9000 μg | 0 |
| LL2-ONCONASE ® | 500 μg | 40% |

In SCID mice implanted intravenously with 5×10⁶ Daudi B lymphoma cells, LL2-ONCONASE® injected intraperitoneally proved to prolong the lives of the mice compared to mice treated with phosphate buffered saline (PBS) or with monoclonal antibody LL2 alone. FIG. 7 shows that all animals treated with PBS developed severe B-cell lymphoma and were sacrificed by day 35. All of the animals treated with LL2 were sacrificed by day 37 due to lymphoma. On the other hand, all of the animals treated with the immunotoxin survived through day 37. The last animal treated with immunotoxin was sacrificed on day 46.

Figure 8:
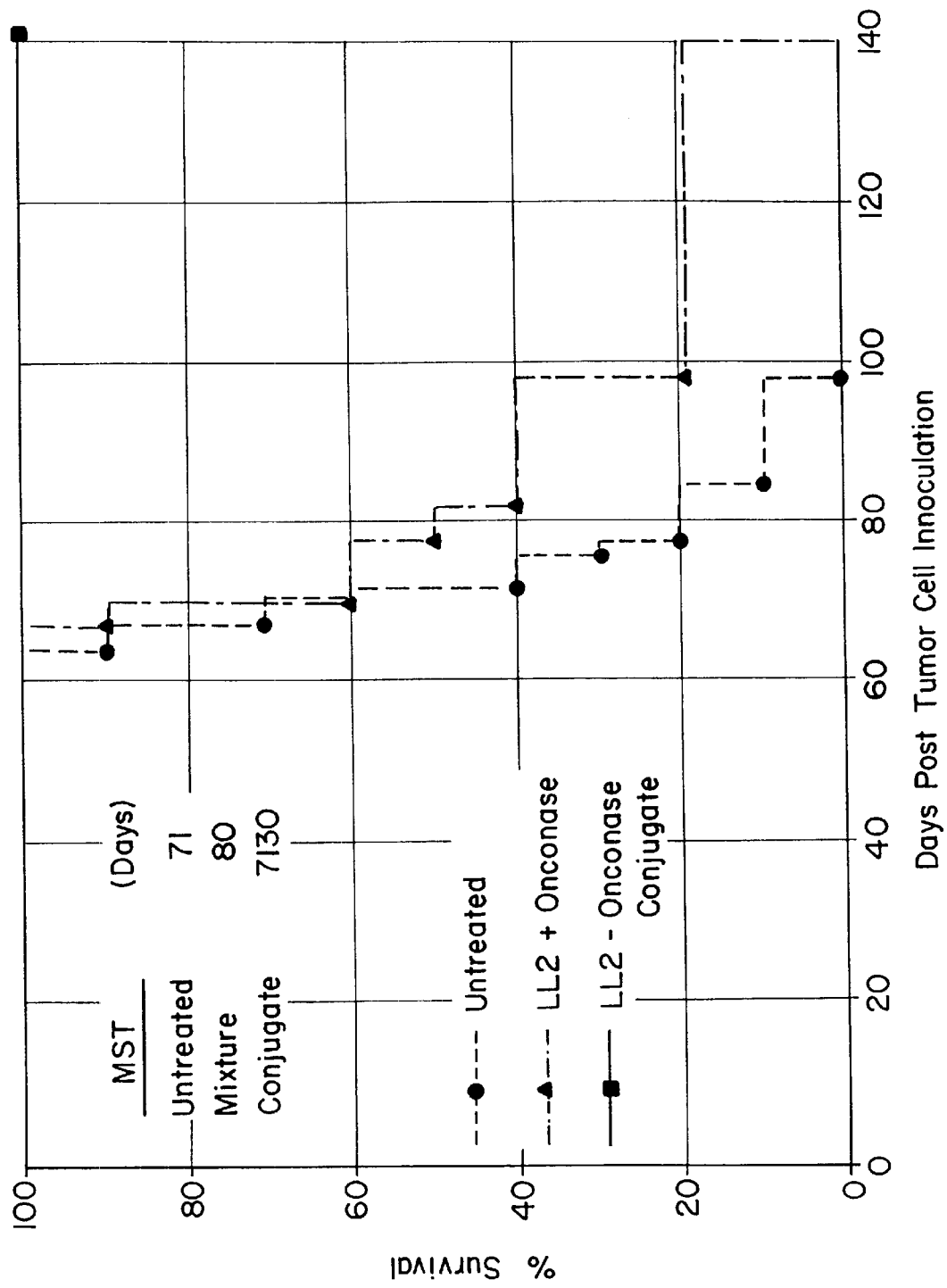
FIG. 8 is a survival graph showing that LL2-ONCONASE® completely protected SCID mice from an intraperitoneal implantation of $2 \times 10^6$ of Daudi cells. The mice were treated 24 hours after implantation with 500 μg of indicated compounds; 100 μg every day for 5 days.

FIG. 8 shows that SCID mice implanted intraperitoneally with 2×10⁶ Daudi cells and then treated with 500 μg LL2-ONCONASE® intraperitoneally, 100 μg per dose per day, survived for over 100 days. The cohort of animals treated with PBS, and unconjugated LL2 and ONCONASE® showed some indication of disease within that time frame. The mean time of survival for the PBS control group was 71 days, for the LL2+ONCONASE®, the mean time for survival was 80 days and the LL2-ONCONASE® treated mice survived longer than 112 days.

Figure 9:
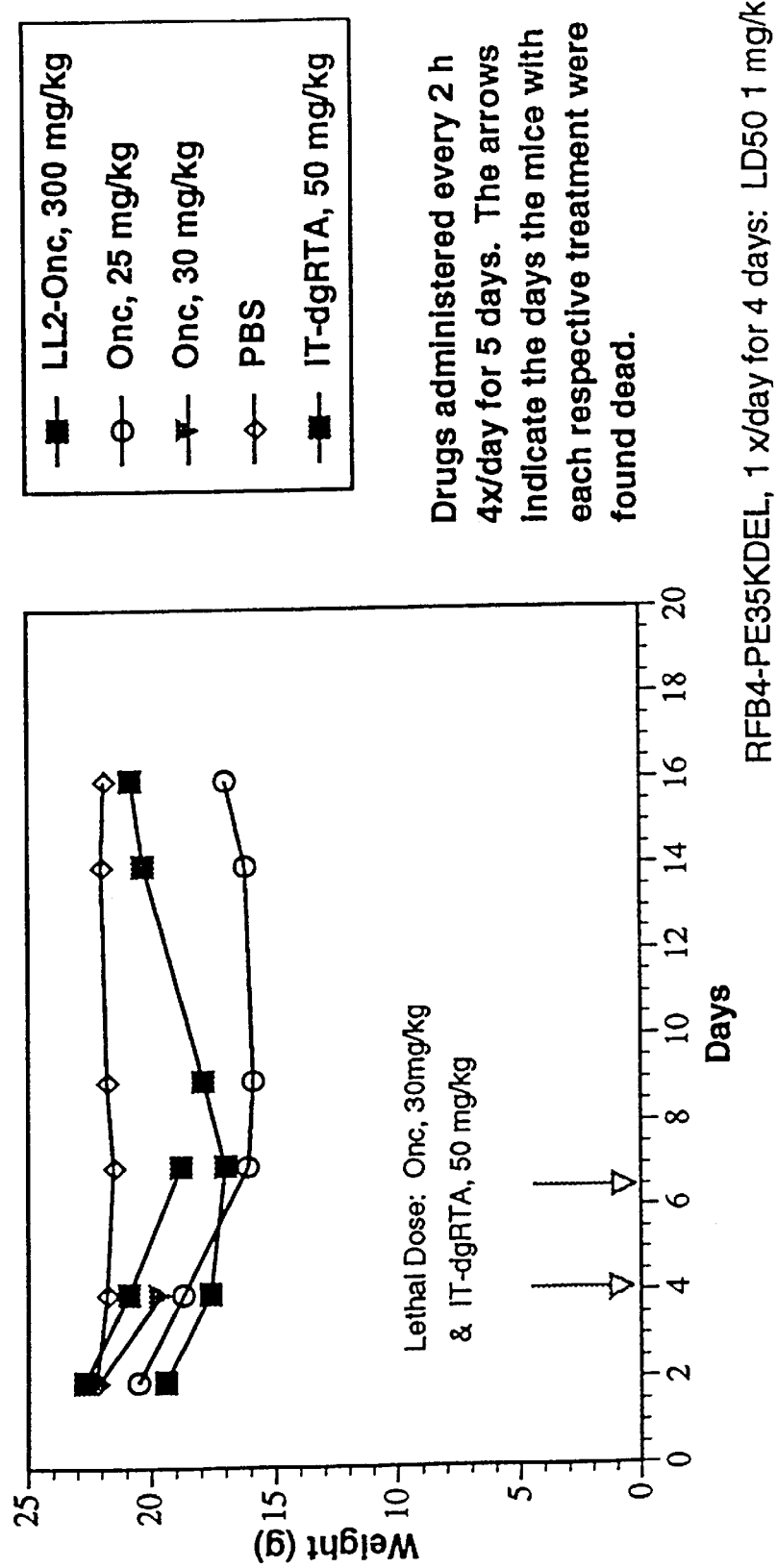
FIG. 9 represents the decreased toxicity of the LL2-ONCONASE® immunotoxin when compared to ONCONASE® alone and IT-dgRTA (RFB4-deglycosylated Ricin A chain). The drugs were administered every 2 hours. 4×/day for 5 days. The arrows indicate the days the mice with each respective treatment were found dead, i.e., the mouse treated with 30 mg/kg ONCONASE® was found dead on day 4 and the mouse treated with 50 mg/kg IT-dgRTA was found dead on day 7.

Finally, FIG. 9 indicates that LL2-ONCONASE® is less toxic than ONCONASE® alone or RFB4-deglycosylated Ricin A chain. Compared to a lethal dose of 30 mg/kg ONCONASE®, the mouse treated with 300 mg/kg LL2-ONCONASE® not only survived but gained weight during the course of the experiment. RFB4, when conjugated to a Pseudomonas exotoxin fragment, had an $LD_{50}$ of 1 mg/kg in a murine model wherein the immunotoxin was given only once per day (Mansfield, et al, *Bioconj. Chem.* 7:557 (1996)).

These in vivo results indicate that LL2-ONCONASE® is a superior B cell toxin compared to ONCONASE® alone, LL2 alone and immunotoxins of LL2-Pseudomonas exotoxin and LL2-doxorubicin. The toxicity studies show that LL2-ONCONASE® is tolerated well with little, if any, side effects.

All publications, including patents and patent applications, mentioned herein above are hereby incorporated by reference.

The foregoing invention has been described in some detail for purposes of clarity and understanding. It will also be obvious that various combinations in form and detail can be made without departing from the scope of the invention.

What is claimed is:

1. A method of killing malignant B cells comprising: contacting a population of human malignant B cells with a selective cytotoxic reagent comprising an onc protein having measurable ribonucleolytic activity covalently linked to an antibody directed against a cell surface marker present on the B cells, wherein the cytotoxic reagent is at least 100 times more cytotoxic to target cells bearing a B cell marker than a comparison reagent comprised of the same antibody joined to the human non-toxic RNase eosinophil-derived neurotoxin (EDN); and thereby killing the human malignant B cells.

2. The method of claim 1, wherein the amino acid sequence of the onc protein is the sequence set out in SEQ ID NO:1.

3. The method of claim 1, wherein the onc protein is produced by recombinant means.

4. The method of claim 3, wherein the amino acid sequence of the onc protein is the sequence set out in SEQ ID NO:1.

5. The method of claim 3, wherein the onc protein is encoded by a nucleic acid molecule identified as SEQ ID NO:2.

6. The method of claim 1, wherein the cell surface marker is CD22.

7. The method of claim 6, wherein the antibody is LL2.

8. The method of claim 1, wherein the cell surface marker is CD74.

* * * * *

UNITED STATES PATENT AND TRADEMARK OFFICE
CERTIFICATE OF CORRECTION

PATENT NO. : 6,395,276 B1 Page 1 of 1
DATED : May 28, 2002
INVENTOR(S) : Susanna M. Rybak, Dianne L. Newton and David M. Goldenberg It is certified that error appears in the above-identified patent and that said Letters Patent is hereby corrected as shown below:

<u>Title page,</u>
Item [73], Assignee, before "Immunomedics, Inc." insert:

-- The Government of the United States of America as represented by the Secretary of the Department of Health and Human Services, and --

Signed and Sealed this

Seventeenth Day of December, 2002

JAMES E. ROGAN
*Director of the United States Patent and Trademark Office*